US010053445B2

United States Patent
Schwarz et al.

(10) Patent No.: US 10,053,445 B2
(45) Date of Patent: Aug. 21, 2018

(54) PHOTOCLEAVABLE CHEMICAL INDUCERS OF DIMERIZATION (CID) AND METHODS OF USE

(71) Applicants: Children's Medical Center Corporation, Boston, MA (US); President and Fellows of Harvard College, Cambridge, MA (US)

(72) Inventors: Thomas L. Schwarz, Newton, MA (US); Matthew R. Banghart, Boston, MA (US); Amos Gutnick, Brookline, MA (US)

(73) Assignees: Children's Medical Center Corporation, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/031,628

(22) PCT Filed: Oct. 24, 2014

(86) PCT No.: PCT/US2014/062115
§ 371 (c)(1),
(2) Date: Apr. 22, 2016

(87) PCT Pub. No.: WO2015/061652
PCT Pub. Date: Apr. 30, 2015

(65) Prior Publication Data
US 2016/0272618 A1    Sep. 22, 2016

Related U.S. Application Data

(60) Provisional application No. 61/895,747, filed on Oct. 25, 2013.

(51) Int. Cl.
| | | |
|---|---|---|
| *A01N 43/54* | (2006.01) |
| *A61K 31/505* | (2006.01) |
| *C07D 401/12* | (2006.01) |
| *C07D 401/14* | (2006.01) |
| *C07D 405/14* | (2006.01) |
| *C07D 239/47* | (2006.01) |
| *C07D 239/49* | (2006.01) |
| *C07D 473/18* | (2006.01) |
| *A61K 41/00* | (2006.01) |
| *C07F 15/00* | (2006.01) |

(52) U.S. Cl.
CPC ........ *C07D 401/12* (2013.01); *A61K 41/0042* (2013.01); *C07D 239/47* (2013.01); *C07D 239/49* (2013.01); *C07D 401/14* (2013.01); *C07D 405/14* (2013.01); *C07D 473/18* (2013.01); *C07F 15/0053* (2013.01)

(58) Field of Classification Search
None
See application file for complete search history.

(56) References Cited

U.S. PATENT DOCUMENTS 7,230,101 B1 * 6/2007 Murthi ................ C07D 475/08
544/260

OTHER PUBLICATIONS

Erhart, Dominik et al., "Chemical Development of Intracellular Protein Heterodimerizers", Chemistry & Biology, Apr. 2013, vol. 20, pp. 549-557.
Umeda, Nobuhiro, et al., "A Photocleavable Rapamycin Conjugate for Spatiotemporal Control of Small GTPase Activity", J. Am. Chem. Soc. 2011, vol. 133, pp. 12-14.
Putyrski, Mateusz, et al., "Protein translocation as a tool: The current rapamycin story", FEBS Letters 586 (2012), pp. 2097-2015.
International Search Report issued in corresponding International Application No. PCT/US2014/062115, dated Feb. 4, 2015, 3 pages.
Written Opinion issued in corresponding International Application No. PCT/US2014/062115, dated Feb. 4, 2015, 6 pages.

* cited by examiner

*Primary Examiner* — Jeffrey H Murray
(74) *Attorney, Agent, or Firm* — Mintz Levin Cohn Ferris Glovsky and Popeo, P.C.; Peter F. Corless

(57) ABSTRACT

The instant invention provides photolysable compounds, and their use in reversible chemical induced dimerization and light-induced regulation of proteins.

20 Claims, 12 Drawing Sheets

FIG. 6B

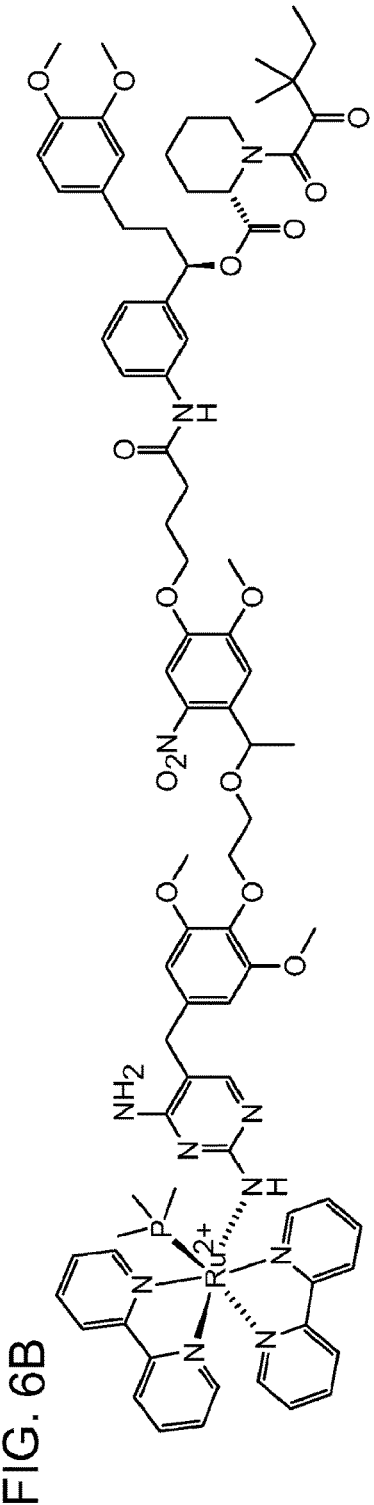

RuBi-TMP-DMNB-SLF (cleaved with 450-500 nm light to remove the RuBi group, followed by cleavage of the DMNB group with 405 nm light; see, e.g., Rial Verde EM et al, Front. Neural Circuits. 2008, 13,2:2; Filevich O. and Etchenique R, Photochem. Photobiol. Sci. 2013, 12, 1565.)

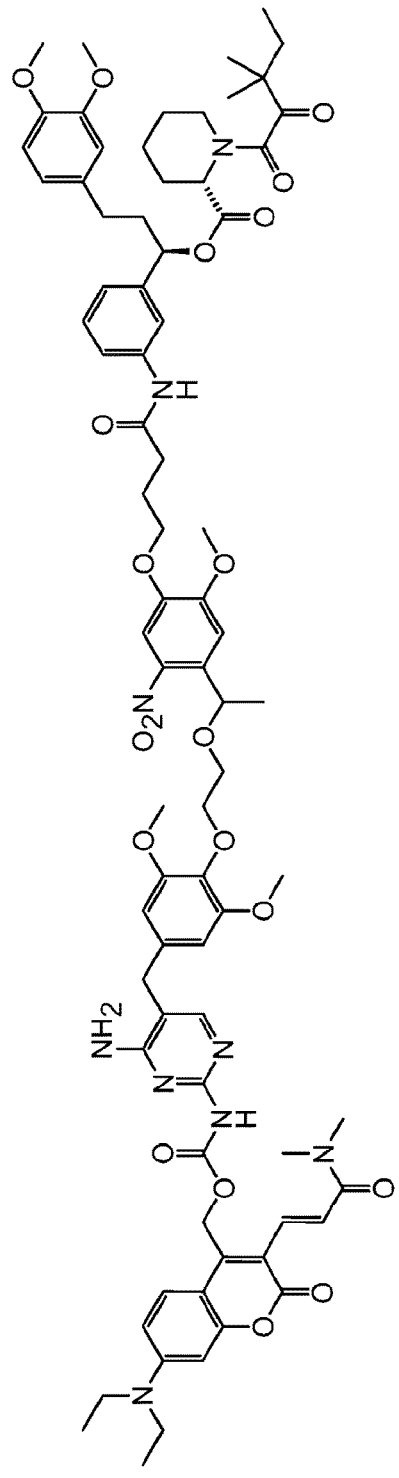

DEAC450-TMP-DMNB-SLF (cleaved with 450-500 nm light to remove the DEAC450 group, followed by cleavage of the DMNB group with 405 nm light; see, e.g., Olson J. et al, J. Am. Chem. Soc., 2013, 135 (16), pp 5954–5957; Olson J, Banghart M. et al, J. Am. Chem. Soc., accepted for publication).

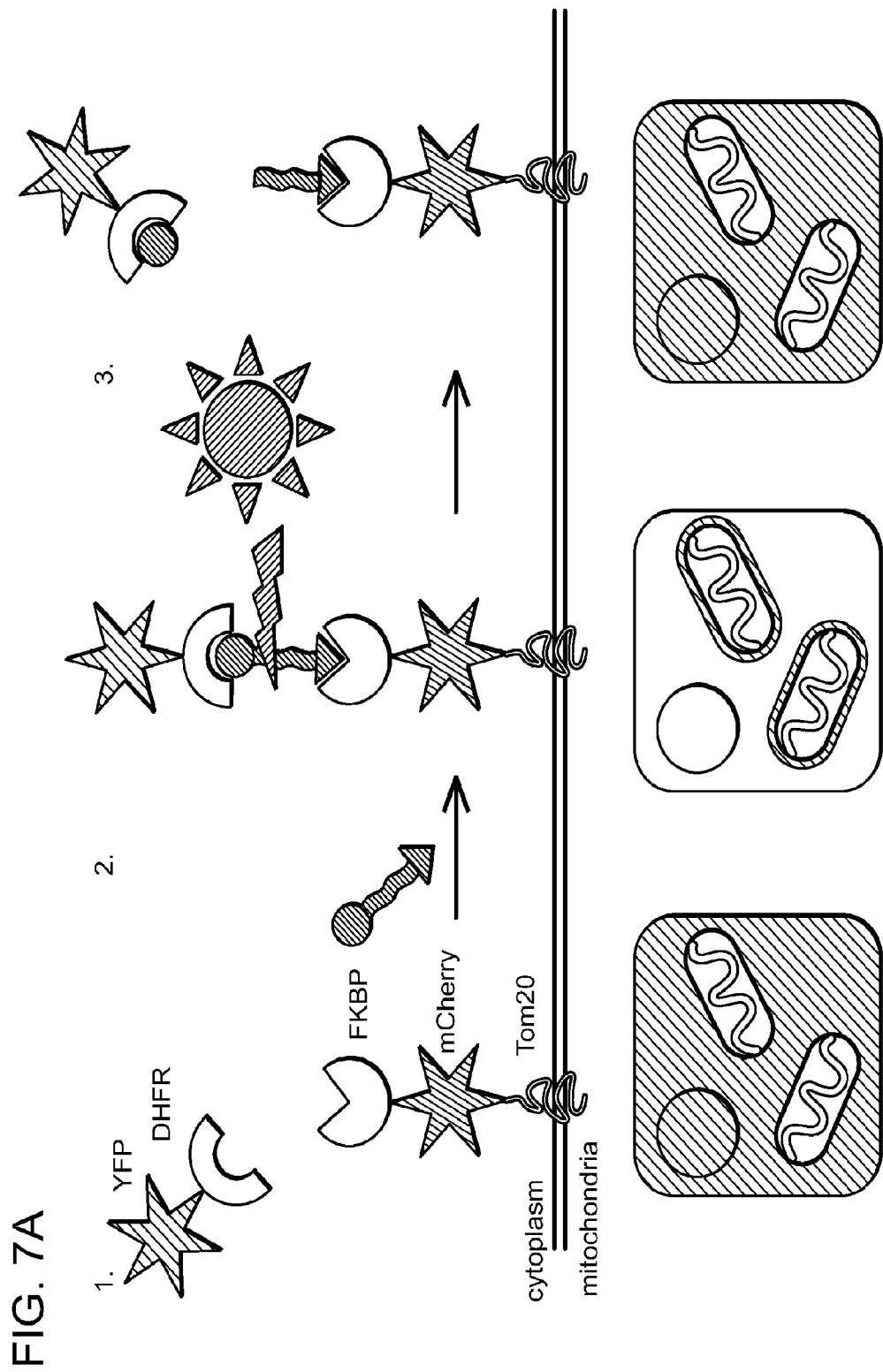

PHOTOCLEAVABLE CHEMICAL INDUCERS OF DIMERIZATION (CID) AND METHODS OF USE

RELATED APPLICATIONS

This application is the U.S. national stage pursuant to 35 U.S.C. § 371, of United States international application Ser. No. PCT/US2014/062115 filed Oct. 24, 2014 and published in English on Apr. 30, 2015 as publication WO2015/061652 A1, which claims the benefit under 35 U.S.C. § 119(e) of U.S. provisional patent application No. 61/895,747, entitled "Photocleavable Chemical Inducers of Dimerization (CID) and Methods of Use", filed Oct. 25, 2013. The entire contents of the aforementioned patent applications are incorporated herein by this reference.

STATEMENT OF RIGHTS TO INVENTIONS MADE UNDER FEDERALLY SPONSORED RESEARCH

This work was supported by the following grant from the National Institutes of Health/National Institute of Neurological Disorders and Stroke: R21NS087582. The government has certain rights in the invention.

BACKGROUND

The widespread need to inactivate a protein in its cellular context is reflected in the degree to which the research community has embraced RNAi technology. But RNAi constructs, even when effective, can be slow to take effect as they depend on the turnover of pre-existing protein. As the protein levels in the cell decline, the cell may die or compensatory mechanisms may be activated. In many instances, it would be desirable to rapidly inactivate a protein with minimal side effects on other cellular components.

Light-triggered methods have been developed in several labs. Examples of light-based methods for protein inactivation include CALI and FAL1 (Chromophore or Fluorophore-Assisted Laser Inactivation) in which an illuminated fluorophore produces a local shower of reactive oxygen species to damage the protein to which it is attached (1). However, the method may not be fully effective and may cause collateral damage to proteins in close proximity (2). Therefore other methods are in development including light-dependent uncaging of inhibitory drugs and methods that harness the light-induced conformational changes of LOV domains to regulate a coupled protein or peptide (3). However, of the available approaches, no single method will meet all needs Inhibitors are not available for many cellular proteins and not all proteins will be susceptible to photo-regulation when coupled to an LOV domain. Another approach has been to convey pharmacological sensitivity on a protein by coupling it to a peptide sequence or domain that is sensitive. Introduction of the target sequence for Hepatitis C Virus NS3 Protease, for example, may sensitize a protein to expression of this protease; which can itself be regulated by inhibitory drugs (4).

Proteins may be coupled to binding sites for high-affinity ligands that will cause them to be dimerized or selectively localized to a designated subcellular compartment. Many Chemical Inducers of Dimerization (CID) have been developed and used to cross-link or localize proteins in the cell. These CIDs include FK1012 (5, 6), rapamycin (6), AP21967 (7) and iRAP (8) and can induce either homodimerization or heterodimerization and thereby activate or inactivate certain proteins or promote their degradation. CIDs have been adopted for a broad array of cellular components because they can be applied to any protein that can tolerate the addition of the necessary binding sites. However, not all proteins can be controlled in this fashion; success depends on whether the dimerization successfully alters the function of the protein. The time course of their action depends on the rate at which they will enter the cell and reversal of the drug requires slow washout and/or competition with a monovalent ligand.

There is a need in the art for an agent that allows for modulation of protein activity with minimal side effects on other cellular components.

SUMMARY

The present invention is directed, at least in part, to dimerizing agents that are cleavable with light, and methods of using such agents to control the function of proteins within a cell. In the present invention, a third element has been inserted between two ligands that can be cleaved by light to split the two ligand groups apart. A purpose of the novel compounds described herein is to gain control of engineered proteins within cells by adding the compound and subsequently inactivating it at will with light. The fact that this is a light-controlled switch means that the experimenter can control precisely when and where in the cell the link is broken. Turning off or removing a protein from a cell is a common strategy for probing the function of a protein or process. Similarly, turning on a protein at will can be a valuable tool for studying its consequences. The compounds of the present invention can be used for either of these purposes and potentially for other forms of regulation of a protein inside a cell.

In one aspect, the invention provides a compound represented by the formula $R^1$—Y—$R^2$, wherein $R^1$ is a ligand capable of selectively binding to a first receptor; $R^2$ is a ligand capable of selectively binding to a second receptor; and Y is a linker providing a covalent linkage between $R^1$ and $R^2$, wherein Y is photocleavable.

In certain embodiments, $R^1$ is a ligand capable the ligand capable of selectively binding to dihydrofolate reductase is trimethoprim (TMP) or a derivative or analog thereof, or methotrexate or a derivative or analog thereof.

In certain embodiments, $R^2$ is a ligand capable of selectively binding to FK506 Binding Protein (FKBP). In certain embodiments, the ligand capable of selectively binding to FK506 Binding Protein (FKBP) is a synthetic ligand for FKBP (SLF) or a derivative or analog thereof.

In certain embodiments, Y is cleavable by exposure to light at a wavelength of about 405 nm. In certain embodiments, Y comprises a dimethoxynitrobenzyl (DMNB) moiety or a derivative or analog thereof.

In another aspect, the invention provides a compound of the invention (e.g., a compound represented by the formula $R^1$—Y—$R^2$, wherein $R^1$ is a ligand capable of selectively binding to a first receptor; $R^2$ is a ligand capable of selectively binding to a second receptor; and Y is a linker providing a covalent linkage between $R^1$ and $R^2$, wherein Y is photocleavable) complexed to (i) a first protein domain comprising a first binding domain and (ii) a second protein domain comprising a second binding domain.

In another aspect, the invention provides a method of regulating activity of a protein, the method comprising:
(a) providing a complex comprising
(i) a first protein domain comprising a first binding domain;

(ii) a second protein domain comprising a second binding domain; and
(iii) a compound of the invention,
wherein the compound of the invention is bound to the first protein domain and the second protein domain;
(b) cleaving the compound of the invention by exposure to light, thereby cleaving the complex and regulating activity of the protein.

In certain embodiments, the first binding domain is dihydrofolate reductase (DHFR). In certain embodiments, the DHFR is *E. coli* DHFR.

In certain embodiments, the second binding domain is FK506 binding protein (FKBP).

In certain embodiments, the first protein domain comprises one domain of an active protein.

In certain embodiments, the second protein domain comprises another domain of an active protein.

In certain embodiments, the first protein domain and the second protein domain together comprise a functional protein.

In certain embodiments, regulating the activity of a protein comprises inactivating the protein.

In certain embodiments, regulating the activity of a protein comprises activating the protein.

In another aspect, the invention provides a method of regulating the activity of a protein in a cell, the method comprising:
(a) providing a cell that expresses a first protein domain comprising a first binding domain and a second protein domain that comprises a second binding domain;
(b) providing the compound of the invention that dimerizes the first and second protein domains; and
(c) cleaving the compound of the invention by exposure to light, thereby cleaving the complex and regulating activity of the protein.

In certain embodiments, dimerization of the first and second protein domains produces an active protein.

In certain embodiments, dimerization of the first and second protein domains inactivates the protein.

Other aspects of the invention are described in, will be apparent from, the following disclosure, and are within the ambit of the invention.

DETAILED DESCRIPTION

Figure 1:
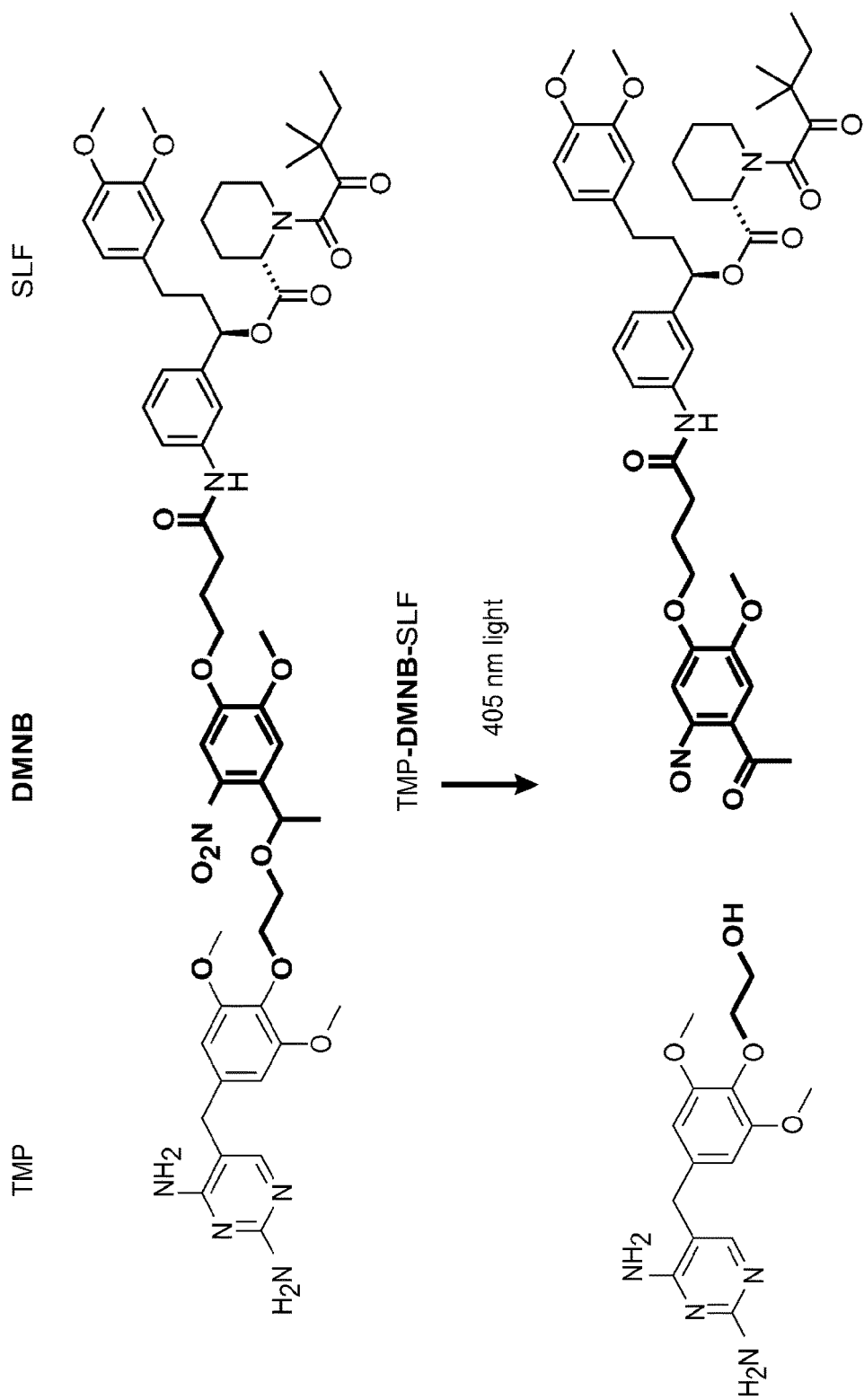
FIG. 1 shows Zapalog (TMP-DMNB-SLF) and its photolysis reaction.

The instant invention describes dimerizing agents that are cleavable with light, and methods of use to control the function of proteins within a cell.

Definitions

The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The term "covalent linkage", as used herein, refers to a linkage between two moieties through one or more covalent bonds, and optionally through one or more atoms. Thus, Y is a photocleavable linker providing a covalent linkage between $R^1$ and $R^2$; the covalent linkage can be broken by exposure to light at an appropriate wavelength.

The term "photocleavable" is meant to refer to a compound or composition that is cleavable by light, i.e., wherein exposure to (absorbance of) light of a suitable wavelength and energy causes the cleavage of one or more covalent bonds. In certain embodiments, the light is in the visible range (e.g., a wavelength or wavelengths from about 390 nm to about 700 nm). In certain embodiments, a photocleavable linker is cleavable by exposure to light at a wavelength of about 400 nm-500 nm, or, more specifically, about 405 nm.

The term "dihydrofolate reductase (DHFR)" is meant to refer to an enzyme that reduces dihydrofolic acid to tetrahydrofolic acid. In certain embodiments, the DHFR is *E. coli*

DHFR. In certain embodiments, the DHFR is a mammalian DHFR, including human DHFR.

The term "trimethoprim" or "TMP" refers to the class of agents known as dihydrofolate reductase inhibitors. Trimethoprim binds to dihydrofolate reductase and inhibits the reduction of dihydrofolic acid (DHF) to tetrahydrofolic acid (THF). By TMP is meant to include variants of TMP with the same or similar activity. The structure of TMP is shown below:

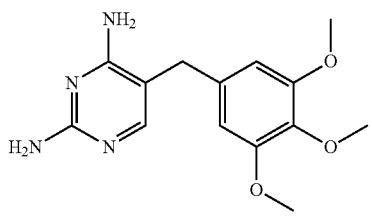 [SMILES: COc1cc(Cc2cnc(N)nc2N)cc(OC)c1OC]

or a derivative (including a bivalent derivative) or analog thereof.

The term "FK506 Binding Protein (FKBP)" refers to a family of proteins that have prolyl isomerase activity and are related to the cyclophilins in function, though not in amino acid sequence. FKBPs have been identified in many eukaryotes from yeast to humans and function as protein folding chaperones for proteins containing proline residues. Along with cyclophilin, FKBPs belong to the immunophilin family. In particular embodiments, the FKBP is FKBP12.

The term "synthetic ligand for FKBP (SLF)" refers to any ligand that binds FKBP. By SLF is meant to include variants of SLF with the same or similar activity. In certain embodiments, the term "SLF" refers to a compound represented by the structure:

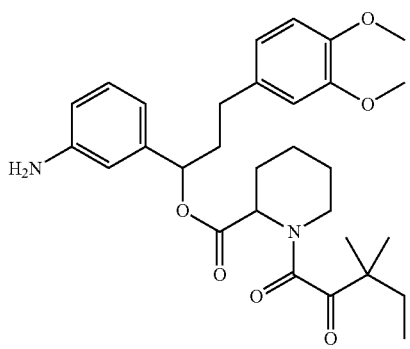 [SMILES: CCC(C)(C)C(=O)C(=O)N1CCCCC1C(=O)OC(CCc1ccc(OC)c(OC)c1)c1cccc(N)c1]

or a derivative or analog thereof.

The phrase "regulating activity of a protein" refers to regulating the activation or inactivation of a protein.

The term "protein domain" refers to a protein, either the entire protein, or a portion thereof.

The term "binding domain" refers to a protein domain that binds a molecule.

The term "dimerization" or "dimerizing" refers to the association of two proteins.

Other definitions appear in context throughout the disclosure.

Compositions

The design of the compounds described herein is based, at least in part, on the following. 1. TMP binds with high affinity to *E. coli* protein Dihydrofolate Reductase (ecD-HFR). 2. SLF binds with high affinity to FK506 Binding Protein (FKBP). Forkhead Binding Protein (FKBP), or FK506 binding protein, is a family of proteins that have prolyl isomerase activity and are related to the cyclophilins in function, though not in amino acid sequence. FKBPs have been identified in many eukaryotes from yeast to humans and function as protein folding chaperones for proteins containing proline residues. Along with cyclophilin, FKBPs belong to the immunophilin family. In preferred embodiments, the FKBP is FKBP12. 3. These small proteins can be fused to selected proteins of interest by genetic engineering and expressed in cells or organisms. 4. If a protein (A) is attached to ecDHFR and a protein (B) is attached to FKBP, then addition of a compound that contains both TMP and SLF can link Protein A to Protein B. 5. Because the TMP and SLF portions of Zapalog are held together by a photolysable group (DMNB), Proteins A and B can subsequently be freed from one another by exposure to light.

In one aspect, the invention provides a compound having the formula:

$$R^1—Y—R^2$$

wherein each of $R^1$ and $R^2$ may be the same or different and each is capable of binding to a receptor which is the same or different; and wherein Y comprises a photocleavable moiety.

In certain embodiments, $R^1$ is capable of binding a first receptor, and $R^2$ is capable of binding to a second receptor. In certain embodiments, each of $R^1$ and $R^2$ is capable of binding to a receptor with a $IC_{50}$ of less than 100 nM. In certain embodiments, each of $R^1$ and $R^2$ is capable of binding to a receptor with a $IC_{50}$ of less than 100 μm, 10 μm, 1 μm, 100 nm or 10 nM. In certain embodiments, each of $R^1$ and $R^2$ is capable of binding to a receptor with a $IC_{50}$ of less than 1 nM.

Each of $R^1$ and $R^2$ may be derived from a compound selected from the group consisting of steroids, hormones, nuclear receptor ligands, cofactors, antibiotics, sugars, enzyme inhibitors, and drugs. Each of $R^1$ and $R^2$ may also represent a compound selected from the group consisting of dexamethasone, 3,5,3'-triiodothyronine, trans-retinoic acid, biotin, coumermycin, tetracycline, lactose, methotrexate, FK506, and FK506 analogs. The binding of $R^1$ and $R^2$ to their respective receptors may be non-covalent or may optionally be covalent, as discussed herein.

In certain embodiments, $R^1$ is a ligand capable of selectively binding to dihydrofolate reductase (DHFR). For example, $R^1$ can be any moiety capable of selectively binding to DHFR, including known DHFR ligands, and derivatives or analogs thereof. The moieties Y and $R^2$ can be selected to avoid interference with the binding of $R^1$ to DHFR; for example, the length of a linker $R^1$ and Y can be varied to optimize binding of $R^1$ to DHFR.

In certain embodiments, $R^1$ is represented by the structure:

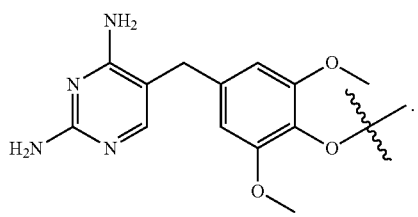 [SMILES: *Oc1c(OC)cc(Cc2cnc(N)nc2N)cc1OC]

In certain embodiments, $R^1$ is a derivative or analog of methotrexate that is capable of binding to DHFR.

In certain embodiments, R² is a ligand capable of selectively binding to FK506 binding protein (FKBP). For example, R² can be any moiety capable of selectively binding to FKBP, including known FKBP ligands, and derivatives or analogs thereof. The moieties Y and R¹ can be selected to avoid interference with the binding of R² to FKBP; for example, the length of a linker R² and Y can be varied to optimize binding of R² to FKBP.

In certain embodiments, R² is represented by the structure:

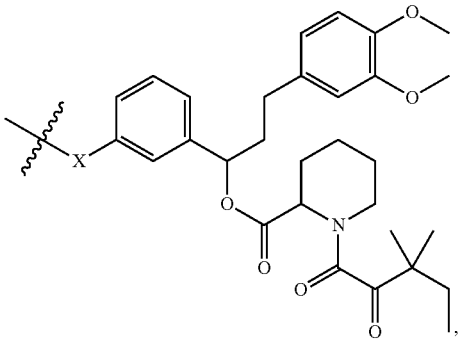

in which X is —O— or —NH—.

In certain embodiments, R² is represented by the structure:

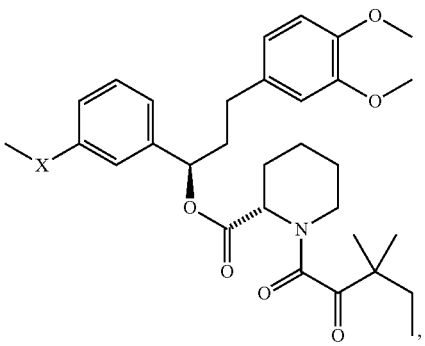

in which X is —O— or —NH—.

In certain embodiments, R² is represented by the structure:

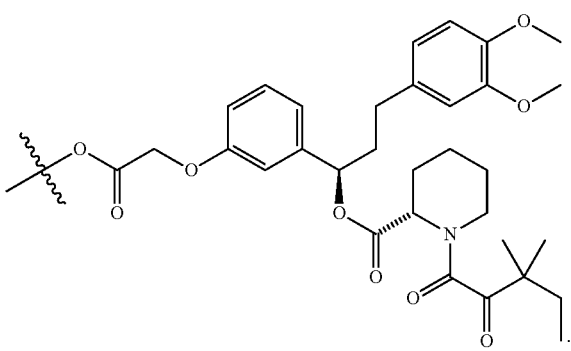

In certain embodiments, R² is represented by the structure (SLF'):

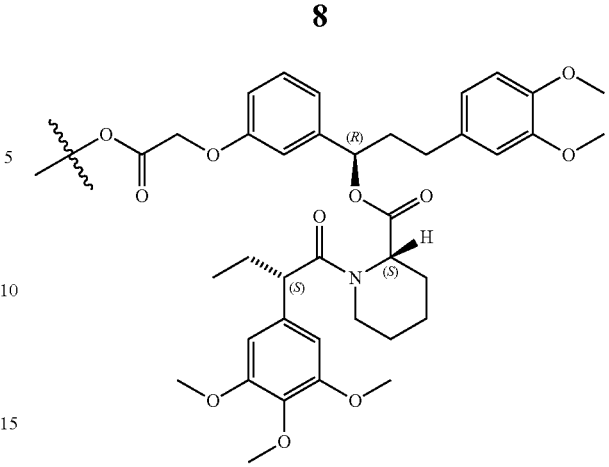

In certain embodiments, R¹ and R² are different.

In certain embodiments, R¹ and R² bind to their respective receptors non-covalently. In certain embodiments, either R¹ or R² (or both) can bind to their respective receptors through a covalent bond. R¹ or R² (or both) can be derivatized with a reactive group capable of chemically reacting with a moiety of their respective receptors to form a covalent bond. Examples of reactive groups include reactive alkenes (such as acrylates), which can react with a nucleophile such as a thiol in a Michael-type reaction (see, e.g., A-TMP-DMNB-SLF and A-TMP-DMNB-Acryl-SLF, FIG. 6); haloalkyl groups, which can react with nucleophiles in a nucleophilic displacement reaction; amines, which can react with electrophiles or with carbonyl groups (e.g., to form Schiff bases); and the like. Additional methods for covalent labeling include the "SNAP-tag" and "CLIP-tag" methods (New England BioLabs) (see, e.g., FIG. 6 for examples), and the "Halotag" systems from Promega (see, e.g., FIG. 6 for an example). There are also covalent labeling techniques based on mutant-lactamases (Watanabe S, Bioconjugate Chem., 2010, 21 (12), pp 2320-2326) and carrier protein (http://burkartlab.ucsd.edu/coa.html).

In certain embodiments, Y is represented by the formula X—Y'—Z, wherein Y' is a photocleavable moiety and each of X and Z may be present or absent and if present, each may be the same or different spacer or linker moiety. Thus, for example, X and Z, if present, may be a linker moiety having from one to 50 atoms in a linker backbone, or one to 25 atoms in a linker backbone, or one to 20 atoms, or one to 15 atoms, or one to 10 atoms, in a linker backbone. Such a linker may comprise, e.g., a $C_1$-$C_{15}$alkylene moiety, a $C_1$-$C_{10}$alkylene moiety or a moiety such as -A-M-A-, in which M is O, S, or NR, R is H or $C_1$-$C_4$alkyl, and each A is independently $C_1$-$C_7$alkylene.

The photocleavable moiety Y or Y' may be any moiety capable of being cleaved by light of a suitable wavelength. Many photocleavable moieties are known in the art; see, for example, V. N. R. Pillai, *Synthesis*, 1 (1980) and V. N. R. Pillai, "Photolytic Deprotection and Activation of Functional Groups," *Org. Photochem.*, 9, 225-323 (1987). Examples of photocleavable moieties include o-nitrobenzyl phenacyl, nitrosulfenyl moieties, nitroindolines, and coumarins, including aminocoumarins. (Coumarin-4-yl)methyl esters (CM-A) are caged compounds that, upon excitation, release the masked biologically active acid HA and the highly fluorescent (coumarin-4-yl)methyl alcohol CM-OH very rapidly and in part with high efficiency. Preferred photocleavable moieties include the dimethoxynitrobenzyl (DMNB) moiety or a derivative or analog thereof. It will be appreciated that many monovalent photocleavable moieties known in the art can be adapted for use as bivalent photocleavable linkers in the compounds of the present invention. For example, a preferred derivative of DMNB is represented by the structure:

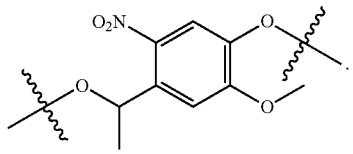 [SMILES: *Oc1cc([N+](=O)[O-])c(C(C)O*)cc1OC]

Further exemplary photocleavable moieties include the following structures:

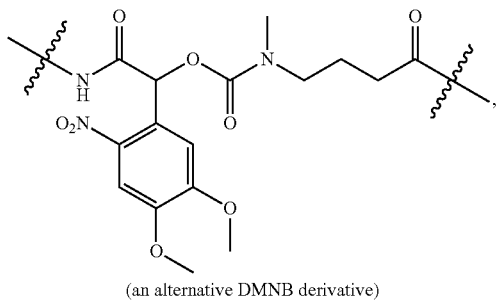
(an alternative DMNB derivative)

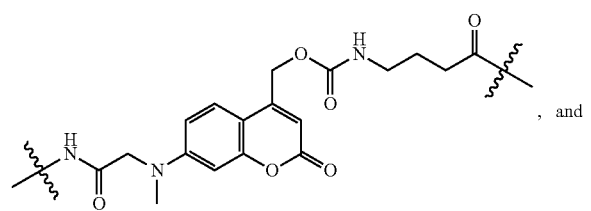
, and

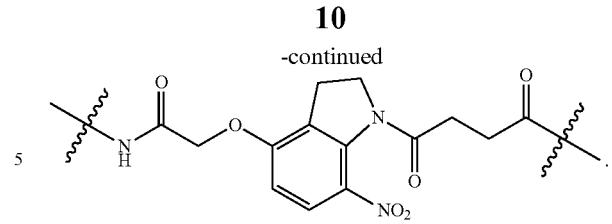

In certain embodiments, the photocleavable moiety Y is cleavable by light capable of penetrating a cell wall, a tissue, or an organ (including skin). In preferred embodiments, the photocleavable moiety Y can be cleaved by a wavelength (or wavelengths) of light which will not cause substantial damage to cells or cellular components such as proteins, nucleic acids, and the like. In certain embodiments, the light is in the visible range (e.g., a wavelength or wavelengths from about 390 nm to about 700 nm). In certain embodiments, a photocleavable linker is cleavable by exposure to light at a wavelength of about 400 nm-500 nm, or, more specifically, about 405 nm. The photocleavable linker preferably has a high quantum yield for photochemical cleavage. The light may be supplied by any light source known in the art, e.g., sunlight, incandescent bulb, fluorescent bulb, halogen bulb, light-emitting diode, laser, and the like. In certain embodiments, the photocleavable linker may be cleaved by two-photon activation with IR or near-IR wavelengths, which permits three-dimensional spatial specificity in depth in tissue. Exemplary moieties capable of two-photon photolysis include nitroindolines and aminocoumarins (see, e.g., FIG. 6).

In certain embodiments, Y may be cleavable by an enzyme selected from the group of enzymes consisting of transferases, hydrolases, lyases, isomerases, and ligases.

In preferred embodiments, the compounds of the invention are cell-permeable. In preferred embodiments, the compounds of the invention are not significantly toxic to cells (e.g., to cells in culture or in vivo). In preferred embodiments, the moieties $R^1$ and $R^2$ are selected to lack an endogenous protein target in a cell or organism of interest.

In one embodiment, the compound $R^1$—Y—$R^2$ is represented by the structure (Compound 1):

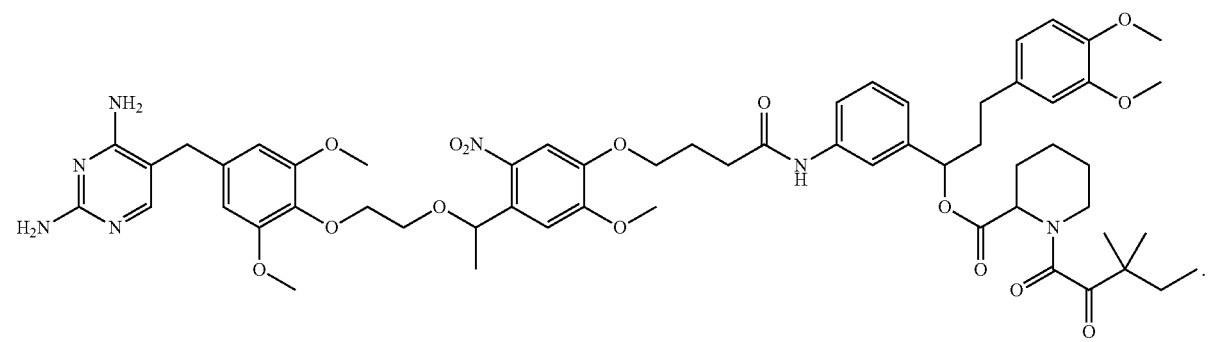 [SMILES: CCC(C)(C)C(=O)C(=O)N1CCCCC1C(=O)OC(CCc1ccc(OC)c(OC)c1)c1cccc(NC(=O)CCCOc2cc([N+](=O)[O-])c(C(C)OCCOc3c(OC)cc(Cc4cnc(N)nc4N)cc3OC)cc2OC)c1]

In another embodiment, the compound R¹—Y—R² is represented by the structure (Compound 1a):

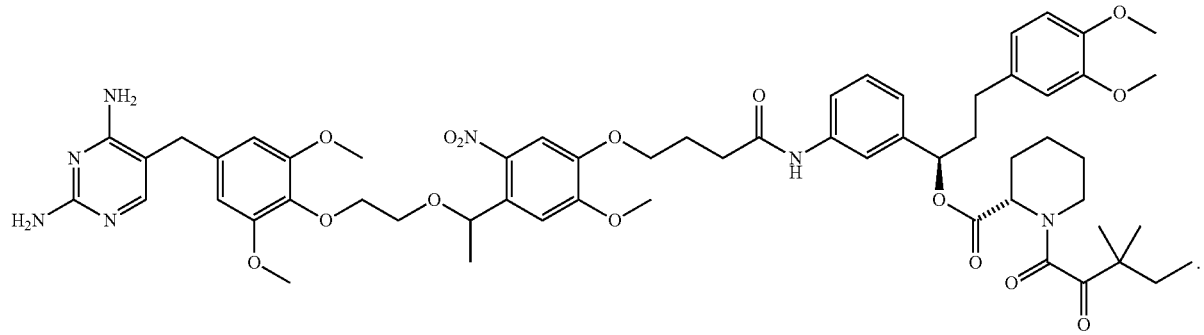

Compounds of the invention can be prepared using a variety of methods, some of which are known in the art. For example, the ligands R¹ and R² can be prepared using conventional methods of synthetic organic chemistry (see, e.g., Michael B. Smith, "March's Advanced Organic Chemistry: Reactions, Mechanisms, and Structure, 7th Edition", Wiley (2013)). Similarly, the photocleavable moiety Y can be prepared according to known methods using no more than routine experimentation. The ligands R¹ and R² can then be coupled to the photocleavable moiety Y to prepare the compound R¹—Y—R².

Thus, for example, Compound 1a can be prepared by the route shown in Scheme 1:

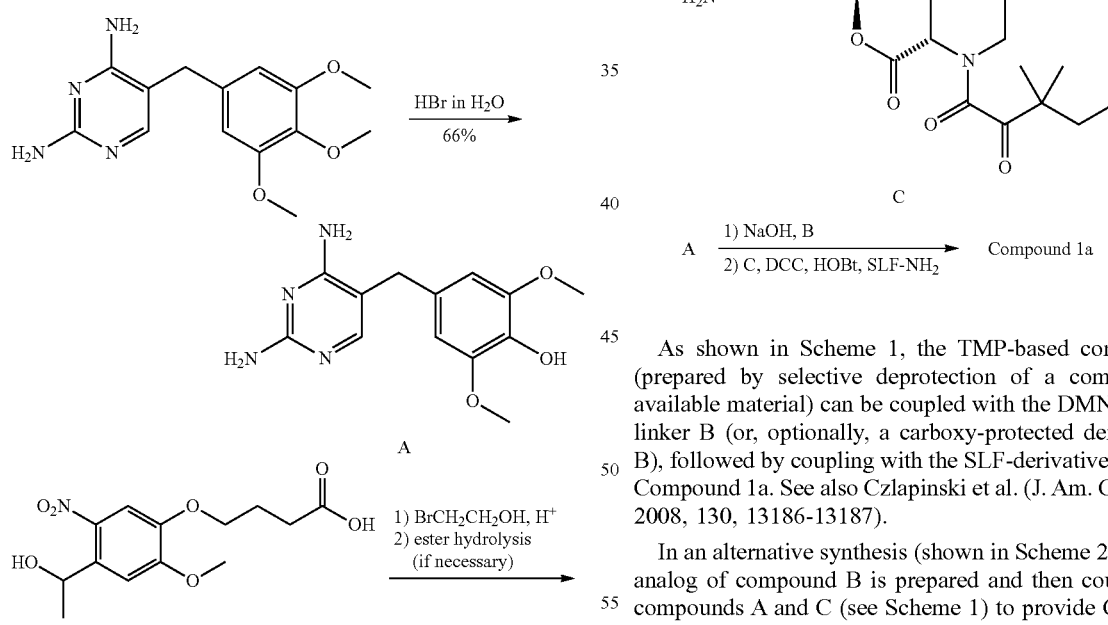

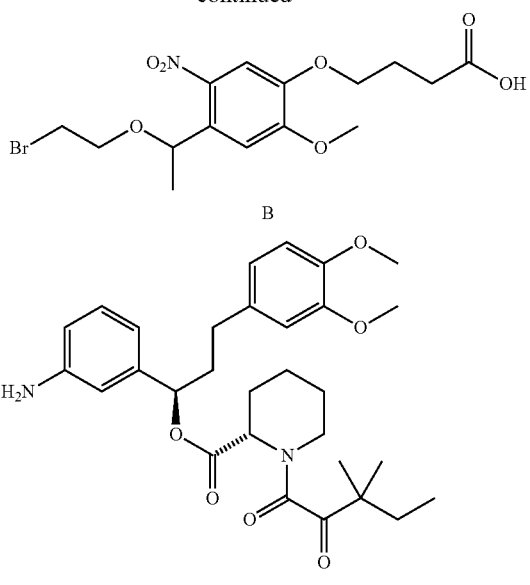

As shown in Scheme 1, the TMP-based compound A (prepared by selective deprotection of a commercially-available material) can be coupled with the DMNB-derived linker B (or, optionally, a carboxy-protected derivative of B), followed by coupling with the SLF-derivative C to yield Compound 1a. See also Czlapinski et al. (J. Am. Chem. Soc. 2008, 130, 13186-13187).

In an alternative synthesis (shown in Scheme 2), the ester analog of compound B is prepared and then coupled with compounds A and C (see Scheme 1) to provide Compound 1a:

Scheme 2

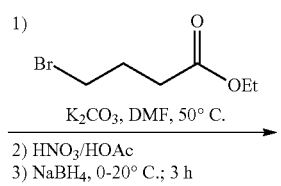

-continued

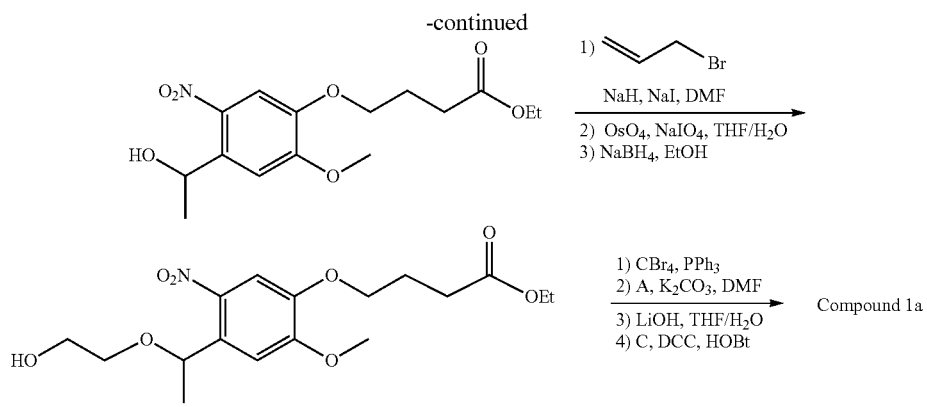

Methods

The present invention features various methods using the photocleavable compounds described herein.

The photocleavable compounds of the present invention can be used in methods to control the function of proteins within a cell. For example, the compounds described herein can be used to inactivate a protein in a cell. To do so, one would engineer the protein to be made as two inactive parts or domains, where one domain is coupled to DHFR, the other domain to FKBP. By domain is meant to refer to a portion of the inactive protein, where together the two domains form an active protein. For example one domain of the two inactive domains could be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the whole protein. The other domain of the two active domains could be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the whole protein. For example, one inactive domain could be 10% of the active protein, and the other inactive domain could be 90% of the active protein, and together the two inactive domains form an active protein. The presence of the photocleavable compounds described herein will bind these two protein domain into a functional whole. Then, at the desired time, a flash of light can be used to break the photocleavable compound apart and thereby sever the link that is preserving the protein in its coupled, functional state.

This method is not limiting, and can be used for any protein that can be made in two inactive domains and have function restored by the DHFR-FKBP bridge.

The photocleavable compounds of the present invention can also be used to activate a protein in a cell. In this case, the targeted protein is first sequestered to an inactive location by the photocleavable compound, and then released to become functional by the photolysis of the compound. The targeted protein contains one of the binding domains for the photocleavable compound (e.g. a binding domain for TMP or SLF). The other domain functions as a receptor for the photocleavable compound; this domain is anchored to the surface of the plasma membrane, mitochondrion, or another cellular location in which the protein cannot perform its normal function. The photocleavable compound will bind the targeted protein to this receptor and thereby hold it inactive until exposure to light breaks the photocleavable compound and allows the targeted protein to move about in the cell.

In certain embodiments, the invention features a method of regulating activity of a protein, the method comprising (a) providing a complex comprising (i) a first protein domain comprising a first binding domain; (ii) a second protein domain comprising a second binding domain; and (iii) a photocleavable compound as described herein, wherein the photocleavable compound is bound to the first protein domain and the second protein domain; and (b) cleaving the photocleavable compound by exposure to light, thereby cleaving the complex and regulating activity of the protein.

In exemplary embodiments, the first binding domain is dihydrofolate reductase (DHFR). DHFR is an enzyme that reduces dihydrofolic acid to tetrahydrofolic acid, using NADPH as electron donor, which can be converted to the kinds of tetrahydrofolate cofactors used in 1-carbon transfer chemistry. In humans, the DHFR enzyme is encoded by the DHFR gene. It is found in the q11→q22 region of chromosome 5. Bacterial species possesses distinct DHFR enzymes (based on their pattern of binding diaminoheterocyclic molecules), but mammalian DHFRs are highly similar. In certain embodiments, the DHFR is $E.\ coli$ DHFR.

In other embodiments, the second binding domain is FK506 binding protein (FKBP).

The invention also features a method of regulating the activity of a protein in a cell, the method comprising (a) providing a cell that expresses a first protein domain comprising a first binding domain and a second protein domain that comprises a second binding domain; (b) providing the photocleavable compound that dimerizes the first and second protein domains; and (c) cleaving the photocleavable compound by exposure to light, thereby cleaving the complex and regulating activity of the protein The first protein domain may comprise one domain of an active protein. The second protein domain may comprise another domain of an active protein. In certain embodiments, the first protein domain and the second protein domain together comprise a functional protein.

In certain embodiments, regulating the activity of a protein comprises inactivating the protein. For example, the compounds of the present invention can be used to inactivate a protein in a cell. In an exemplary embodiment, one would engineer the protein to be made as two inactive halves, one coupled to DHFR, the other to FKBP. The presence of the compound of the invention will bind these two protein halves into a functional whole. The researcher can, at the desired time, use a flash of light to break the compound apart and thereby sever the link that is preserving the protein in its coupled, functional state.

This approach will work on any protein that can be made in two halves and have function restored by the DHFR-FKBP (or other ligands) bridge. As described herein, exemplary classes of proteins include, but are not limited to, enzymes (localization+catalytic domains), transcription Factors (DNA binding+activation domains), motor Proteins (motor+cargo binding domains), receptors (transmembrane & binding+effector domains), and proteinaceous prodrugs.

By forcing the interaction of two inactive parts of a target protein, the photocleavable compounds of the invention offer the ability to generate a recombinant, photo-destructible version of any protein whose functionality can be replicated by dimerization of its inactive parts. For example, by dimerizing an enzyme's localization domain to its catalytic domain, a compound of the invention can be used to generate a functional, photo-destructible enzyme. By dimerizing a transcription factor's DNA-binding domain to its activation domain, a compound of the invention can be used to generate a functional, photo-destructible transcription factor. By dimerizing a kinesin's cargo-binding domain to its motor domain, a compound of the invention can be used to generate a functional, photo-destructible kinesin. By dimerizing a transmembrane receptor's ligand binding and transmembrane domain to its intracellular effector domain, a compound of the invention can be used to generate a functional, photo-destructible transmembrane receptor.

Other examples include ion channels, ionotripic receptors, GPCRs/G-proteins, enzymes that function as multimers or complexes, transcription factors (repressors in particular), kinases, phosphatases, glycotransferases, receptor kinases, transporters, SNARE proteins (exocytosis machinery), endocytic machinery, ion channel modulatory/auxiliary subunits, chaperones, histones, histone-modifying enzymes, genome editing, nucleotide cyclases, nucleotide hydrolases, In other embodiments, a photocleavable dimerizer can be prepared such that both binding domains are identical (e.g., SLF-DMNB-SLF or TMP-DMNB-TMP). Such a compound could be used as a photocleavable homodimerizer. In certain embodiments, this photocleavable homodimerizer could be used to induce dimerization of pairs of molecules of a target protein, then photocleaved to reverse the dimerization. For example, pairs of receptor tyrosine kinase molecules could be forced to dimerize by addition of a photocleavable homodimerizer, causing their forced activation and downstream signaling. Thereafter, the dimerization and resulting activation could be reversed by photocleavage of the photocleavable homodimerizer.

In other embodiments, a compound according to the invention can be used to dimerize proteinacious prodrugs, though either homodimerization or heterodimerization, and allow reversal of the dimerization via photo-cleavage of the compound in vivo.

In other embodiments, regulating the activity of a protein comprises activating the protein. For example, in various situations it is desirable to deliver a biologically active protein through the cell membrane to inner cell structures. It is also desirable to deliver such biologically active proteins to selected cells in a heterogeneous cell population. For example, in treating diseased or infected cells, such as virus-infected cells or transformed or malignant cells, it may be desirable to deliver a biologically active protein to a diseased or malignant cells but not to normal cells. The above-described compounds have considerable therapeutic advantages, for example for cancer therapy where the cell system is accessible to light. As long as the compound is not subjected to UV light, preferably light with a wavelength of 405 nm, the compound is not cleaved. In the absence of UV light, the compounds of the invention are not cleavable to avoid undesired cleavage. Accordingly, the compounds of the present invention allow rapid, nearly quantitative release of the active protein at the particular time when, and the particular place where, the compound is illuminated.

For example, in certain exemplary embodiments, the compounds of the present invention can be used to activate a protein in a cell. This approach will work on any protein that can be activated by photolysis of the compound. In this case, the targeted protein is first sequestered to an inactive location by the compound of the invention, and then released to become functional by photolysis of the compound. The targeted protein contains one of the binding domains of the claimed compound. The other domain of the claimed compound functions as a receptor for the compound; this domain is anchored to the surface of the plasma membrane, mitochondrion, or another cellular location in which the protein cannot perform its normal function.

For example, this domain can be associated with at least one subcellular delivery sequence or signal. For example, the subcellular delivery sequence or signal can mediate localization of the domain that functions as a receptor to a membrane, a mitochondrion, a peroxisome, a nucleus, an endoplasmic reticulum, a Golgi, a vesicle, a lysosome, an endosome, and/or a chloroplast, for example. Thus, the subcellular delivery sequence or signal optionally comprises a mitochondrial matrix-targeting sequence, a nuclear localization signal, a signal peptide, an ER retention signal, a peroxisomal targeting motif, a chloroplast stromal targeting sequence, a transmembrane domain, and/or a lipid attachment site.

The compound of the invention will bind the targeted protein to the receptor and thereby hold it inactive until exposure to light breaks the composition and allows the targeted protein to move about in the cell.

In other embodiments, a peptide/protein domain that is capable of either inhibiting or promoting the activity of a target protein could be a forced to associate with the target protein by it to the one receptor domain as well as tethering the target protein to the other receptor domain, then linking the two with the claimed compound, and finally releasing the inhibitor/activator peptide from the target protein with photolysis of the claimed compound, thereby releasing the target protein from inhibition/activation.

Applications to Split Kinesin System

As an initial use of the compounds of the invention (e.g. "Zapalog") to answer a biological question, the split-kinesin system can be used to examine the interplay of plus-end and minus-end directed motors. An abiding question in cell biology concerns the coordination of the opposing motors when they are on the same cargo vesicle. The "tug-of-war" hypothesis posits that both the plus-end directed kinesin and minus-end directed dynein are simultaneously active and working against one another (18-21). Other models identify switching mechanisms that can selectively activate either the kinesin or dynein (22). In an axon, the interplay of the motors governs whether a cargo moves anterograde (away from the soma) or retrograde (towards the soma). Conflicting evidence for both models has been obtained from force and velocity measurements in vitro and from biochemical studies of motor regulation (21, 23-27). A recent in vitro study on isolated microtubules used DNA origami to engineer cargos with controlled numbers of each motor in a set of "tug of war" competitions (18). This study demonstrated the value of being able to rapidly detach one set of motors to observe the change in transport of the cargo. These experiments left open the question of whether in vivo the same competition occurs. With the compounds of the present invention, this will be addressed by observing the change in behavior of cargos when the kinesin motor is abruptly detached from its cargo by 405 nm light. Does a cargo moving anterograde simply stop or does it immediately reverse direction as the dynein motor is no longer opposed? Does a retrogradely moving cargo continue as before or are its speed and processivity suddenly enhanced by the absence of opposing kinesin? These questions will be addressed with several cargos including the TfR vesicles already discussed, but also with 1) mitochondria (using a split Kinesin-1 heavy chain) as an example of a cargo that contains many copies of each motor (28, 29) and 2) synaptic vesicle precursors (using a split Kif1a).

There are many other potential applications of this method to questions in axonal transport and motor cell biology. In the longer term, the method can be used to answer another controversial point—to what extent does the proper functioning of the retrograde motor in vivo depend on the presence of the anterograde motor (30)? Is the anterograde motor acutely regulating retrograde movement or only necessary for the initial delivery of the retrograde motor to distal regions? Acute disruption of a functioning kinesin may also clarify certain mutant phenotypes for motors in which many cargos accumulate at traffic jams. Are all these cargos directly transported by the mutated motor or do they accumulate only as an indirect consequence of secondary changes to the axon (30)? Another possibility is the construction of a split p150 subunit of dynactin. There are competing models of p150 function: one is that p150 is required for smooth processive movement of the dynein motor: the other is that p150 is only needed to initiate retrograde movement at plus ends (30-33). This issue could be clarified with the compounds of the invention by the rapid detachment of p150 from actively moving organelles.

In adapting for the compounds of the present invention (Zapalog), the previously used TfR-GFP assay for split kinesins, tandem arrays of FKBP or DHFR may need to be analyzed, as discussed herein in Example 3, to optimize movement and processivity. The movements of other axonal cargos will be followed, such as mitochondria labeled with mitodsRed, to determine whether the effect of the laser is selective for the Zapalog cargo or due to non-specific damage to the axon. Levels of expression of the motor and cargo binding domains will be monitored to avoid false negative results due to insufficient expression of either construct or incorrect stoichiometries. For the proposed biological experiments—particularly the test of the "tug-of-war" hypothesis—the endogenous cellular kinesin may complicate the analysis. One solution will be to use RNAi or available knockout mice to remove the endogenous proteins. Alternatively, it may be found that even on a wildtype background, the overexpressed components of the split kinesin displace enough endogenous protein that photolysis of Zapalog will alter the movement of the cargo in an interpretable fashion, i.e. slowing anterograde movement, decreasing anterograde processivity, or altering the balance of anterograde and retrograde motors to allow dynein to predominate.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

The present invention features, in part, compositions and methods to control the function of proteins within a cell by using a dimerizing agent that is cleaved by light. Chemical inducers of dimerization are composed of either two identical ligands joined to one another (homo-dimerizing) or two different ligands joined to one another (heterodimerizers). It is to be understood that the term heterodimerizers can include cyclical heterodimerizers. A novel finding of the present invention has been to insert between the two ligands a third element that can be cleaved by light to split the two ligand groups apart. The particular photo-cleavable chemical inducer of dimerization is named "Zapalog" (TMP-DMNB-SLF), and its structure is described herein. In brief, it consists of trimethoprim (TMP) and SLF (Synthetic Ligand for FKBP) joined by a dimethoxynitrobenzyl (DMNB) linker. This linker can be broken by exposure to 405 nm light. A purpose of the compound is to gain control of engineered proteins within cells by adding the compound and subsequently inactivating it at will with light. The fact that this is a light-controlled switch means that the experimenter can control precisely when and where in the cell the link is broken. Turning off or removing a protein from a cell is a common strategy for probing the function of a protein or process.

Similarly, turning on a protein at can be a valuable tool for studying its consequences. Zapalog can be used for either of these purposes and potentially for other forms of regulation of a protein inside a cell.

Example 1. Design of Zapalog

Figure 2:
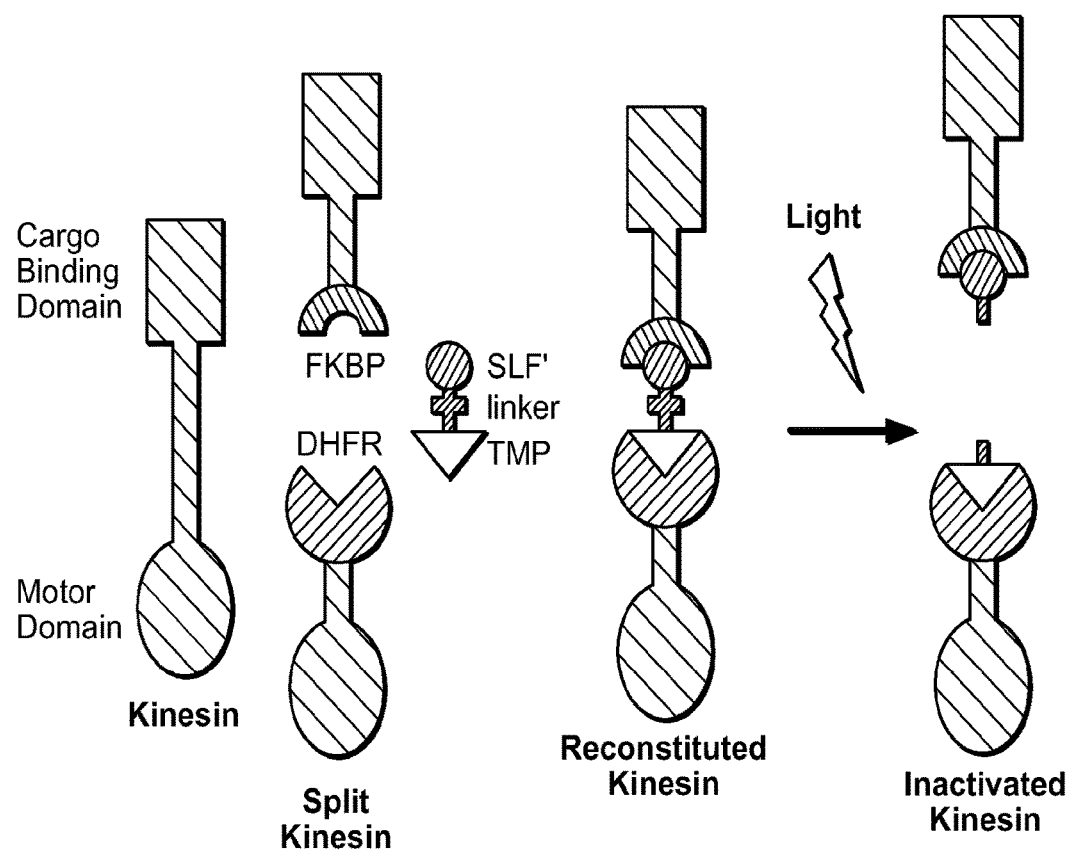
FIG. 2 is a schematic of inactivation of an engineered kinesin by use of a photolysable linker.

The structure of Zapalog is shown in FIG. 1. Zapalog will enable two proteins or domains to be linked. FIG. 2 shows a schematic of the linkage using the example of split kinesin. The trimehtoprim (TMP) portion of Zapalog will bind to the dihydrofolate reductase (DHFR) domain of one chimeric partner while the SLF portion will bind to the FK506 Binding Protein (FKBP) domain in the second chimera. The photosensitive DMNB linker will be broken by 405 nm light, as in FIG. 1.

The parameters that guided the design of Zapalog included the following: 1. Inclusion of two independent ligand moieties to enable heterodimerization of suitably engineered proteins. 2. High specificity and affinity for the binding domains. 3. Lack of endogenous binding partners in mammalian cells. 4. Membrane permeability. 5. A linker that would prevent binding to one end of Zapalog from sterically inhibiting binding to the other end. 6. Photolysis of the linker at a wavelength that would not be highly cytotoxic nor interfere with imaging other common fluorophores. 7. Relative ease of synthesis.

A TMP-SLF linker was developed in the Bertozzi lab at UC Berkeley (9). This compound was successfully used to couple proteins in a yeast 3-hybrid assay and to anchor the catalytic domain of a glycosylating enzyme to a Golgi-resident localization domain. Their work established the cell permeability and efficacy of TMP-SLF as a CID with an EC50 of 45 nM. They also established that neither TMP nor SLF had endogenous protein targets and that TMP-SLF was not toxic to cells even at 1 uM (9). Thus TMP-SLF provides a photo-insensitive control for TMP-DMNB-SLF (Zapalog). TMP and SLF are joined by a simple linear linker; this facilitated introduction of a photo-labile linker which would have been difficult in the cyclic structures of the rapalog family. In addition, the protein domains to which the TMP and SLF ligands will attach are relatively compact (DHFR=158 aa; FKBP=107 aa). Each is approximately half the size of GFP and, given the widespread use of GFP-tags (and YFP tags) on functional proteins, it is likely that, with proper engineering, many proteins will tolerate these domains as well. DMNB was chosen as the photo-labile linker because it has been successfully employed for photo-uncaging of compounds such as glutamate and cAMP (10-12), because it is cleaved by 405 nm of light, a wavelength that will not interfere with GFP or YFP imaging but is long enough to avoid UV damage to proteins, and because it has an excellent photolysis quantum yield and uncaging rate (11). DMNB may also be useful for two-photon photolysis.

Figure 3:
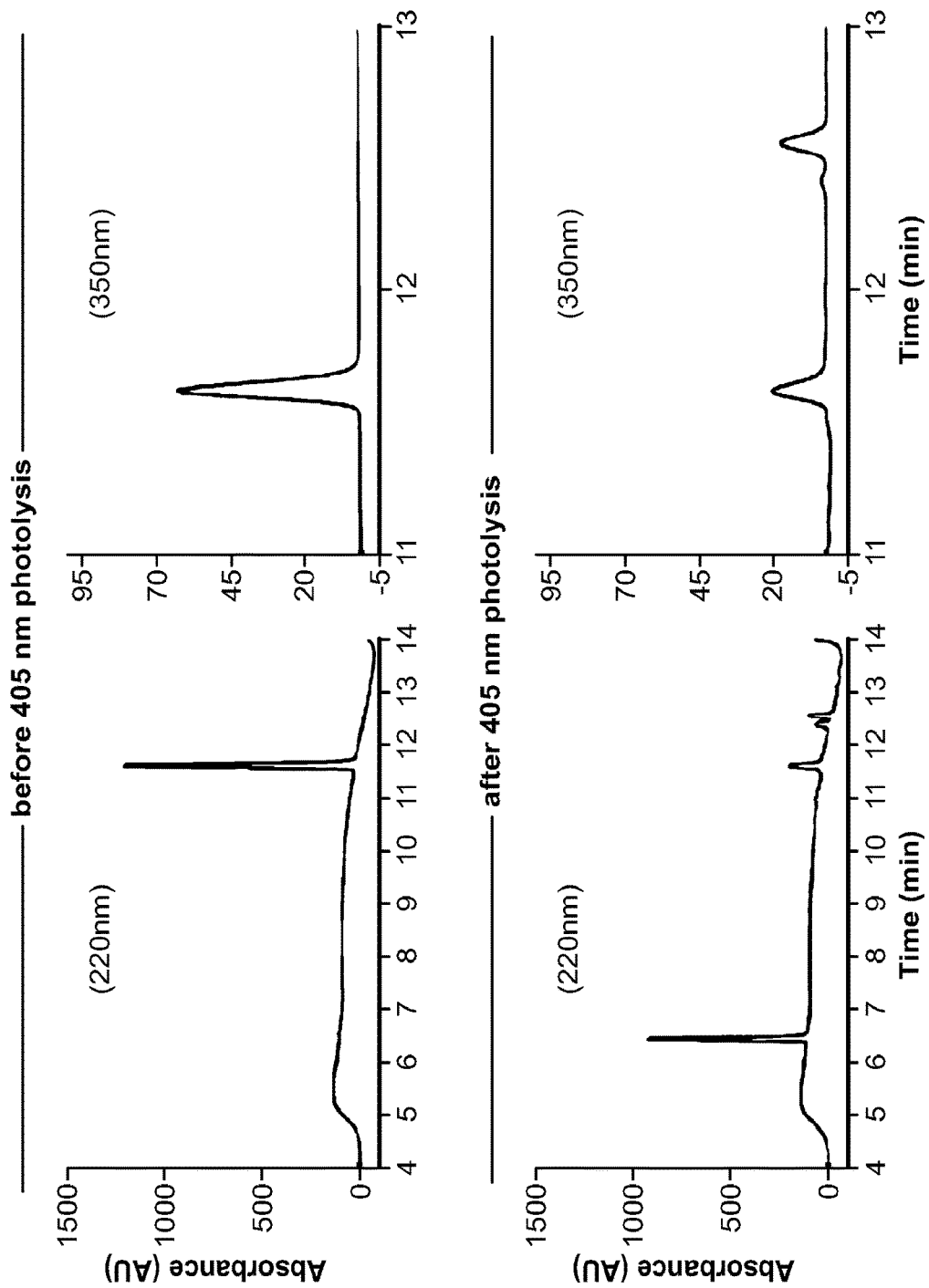
FIG. 3 shows HPLC Analysis of Zapalog before and after photolysis.

Zapalog was synthesized and 10 mg of TLC purified material was determined to be >98% pure by LCMS/HPLC and containing less than 0.1% of the monomeric ligands TMP and SLF. Both the purity and complete photolytic cleavage of Zapalog has been confirmed by HPLC analysis before and after exposure to 405 nm light. As shown in FIG. 3, light converts Zapalog from a single peak that elutes at 11.7 minutes to two peaks that elute at 6.6 (detected by 210 nm absorbance) and 12.6 min (detected at 350 nm).

Figure 4A:
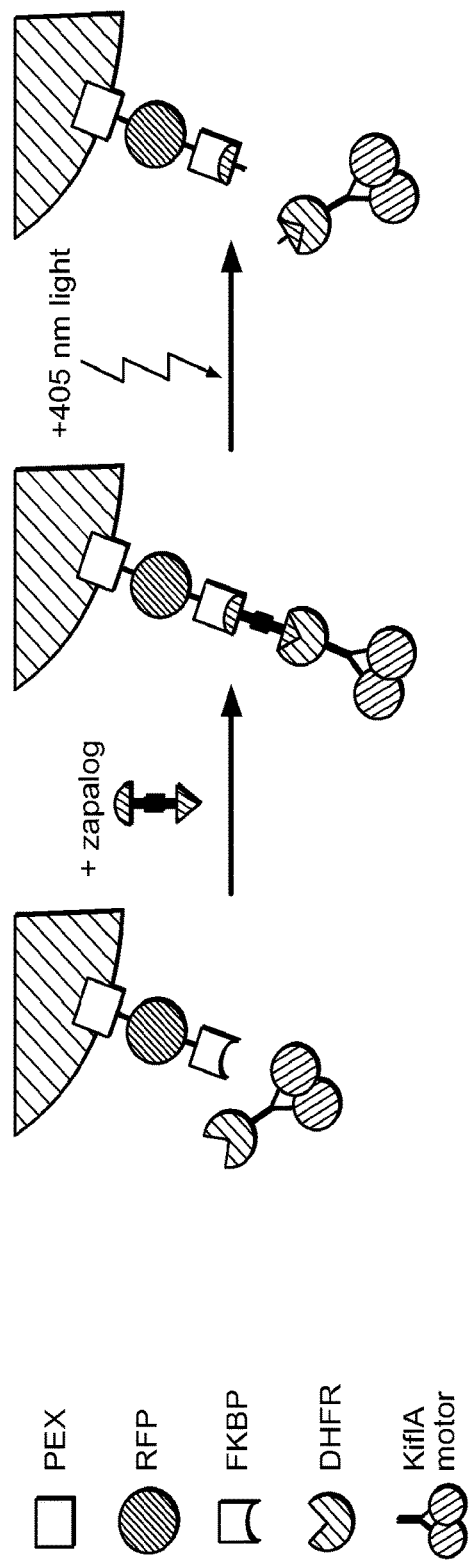
FIG. 4 shows peroxisome redistribution when coupled to a motor domain by Zapalog. The top panel is a schematic of Zapalog induced linkage of a peroxisome localization domain (PEX) to the motor domain of kinesin Kif 1A. The bottom panel shows translocation of motor to peroxisomes and redistribution of peroxisomes when either TMP-SLF or Zapalog are added and reversal of the Zapalog effect by light.
Figure 4B:
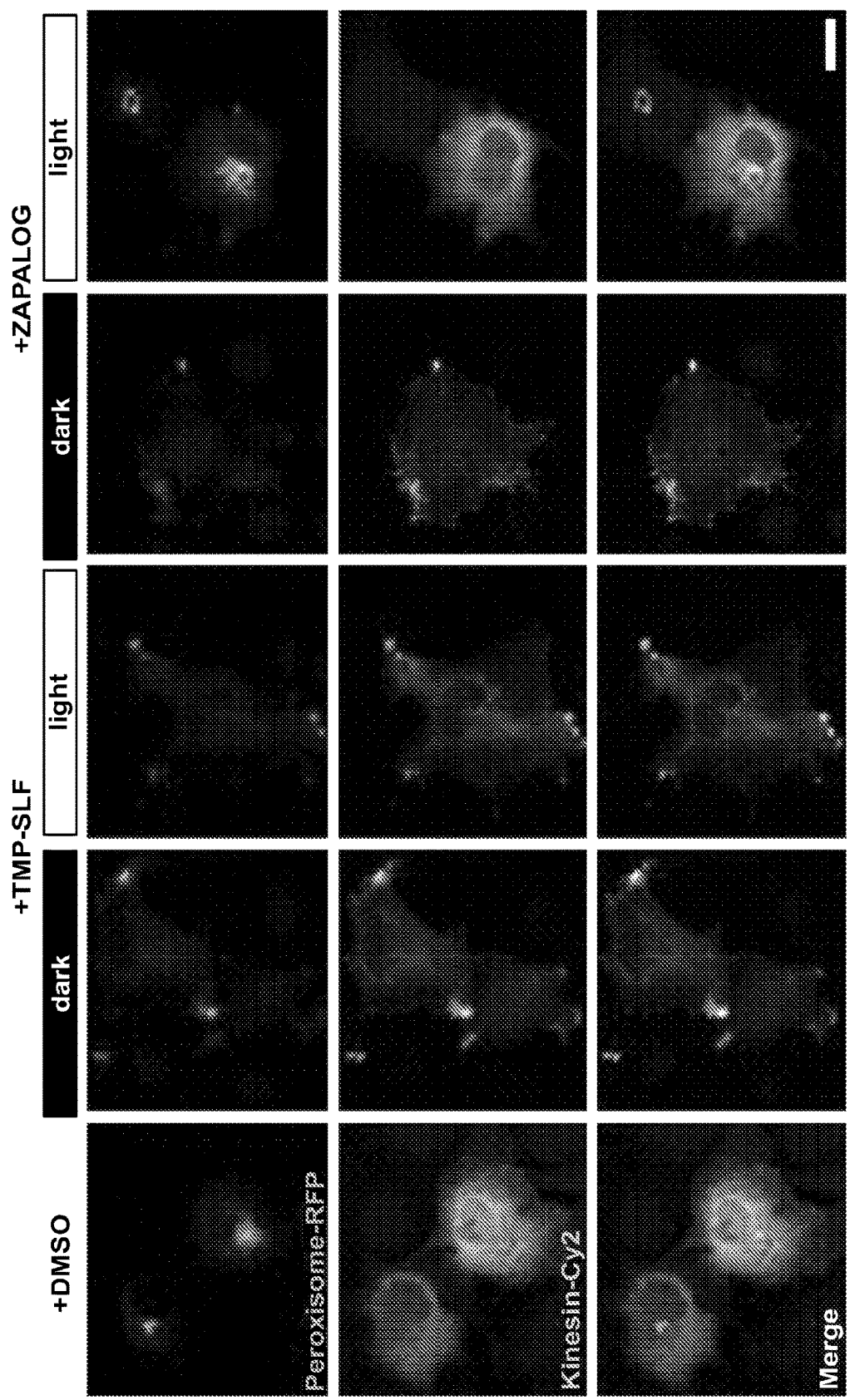
Figure 5:
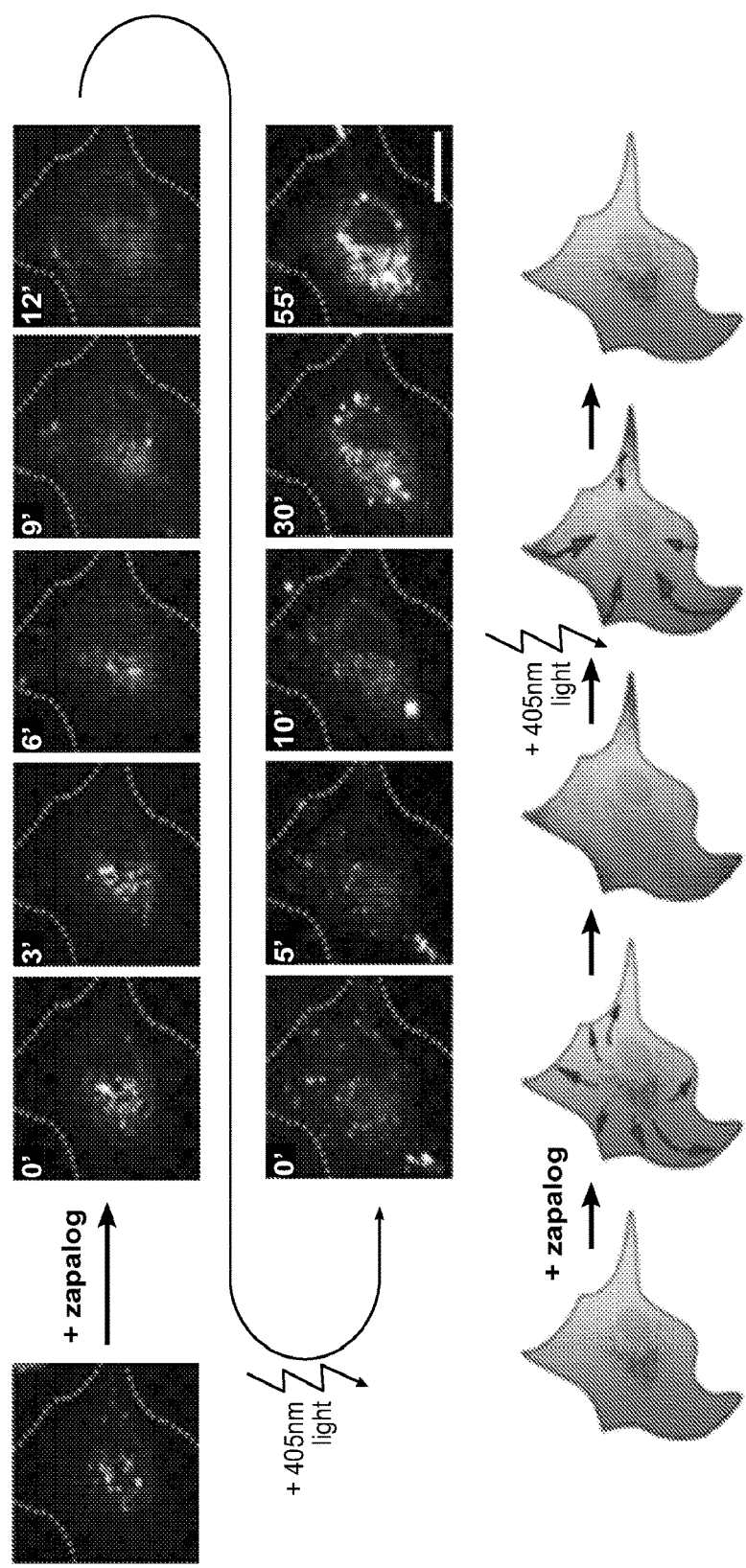
FIG. 5 shows live imaging of Zapalog-induced peroxisome movement and recovery after photolysis. Images at 3 minute intervals are shown.
Figure 6A:
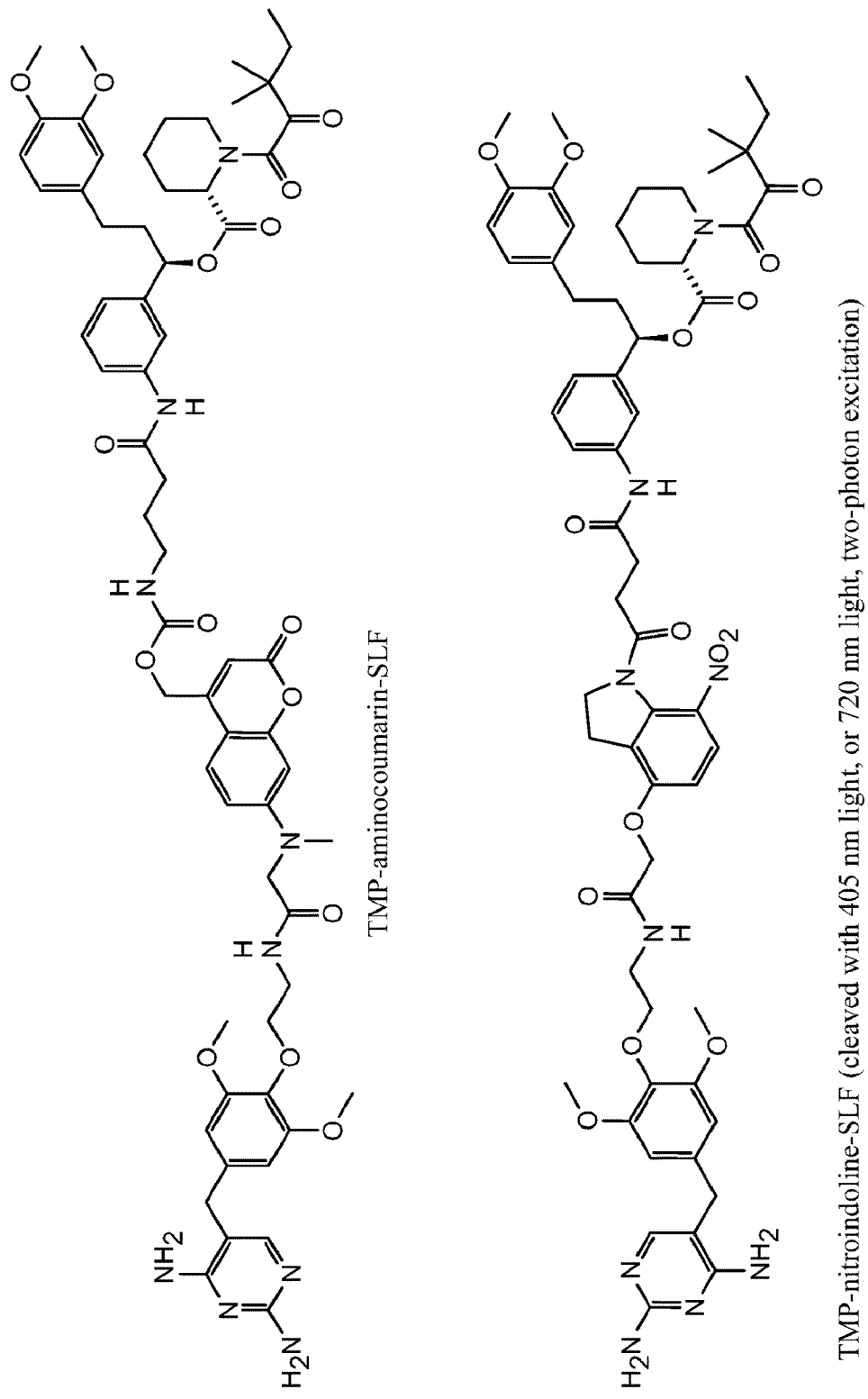
FIG. 6 shows the structures of exemplary photocleavable dimerizing agents according to the invention.
Figure 6C:
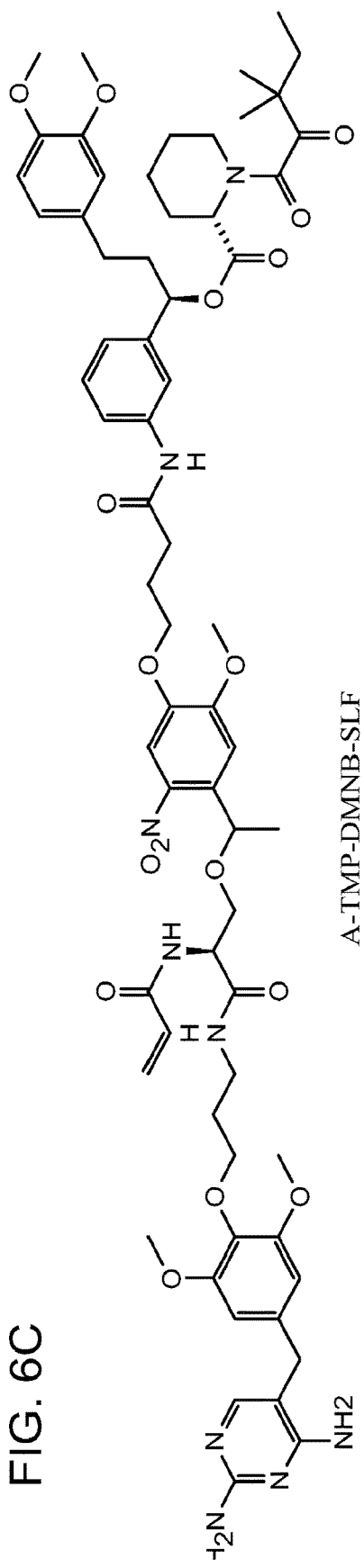
Figure 6C:
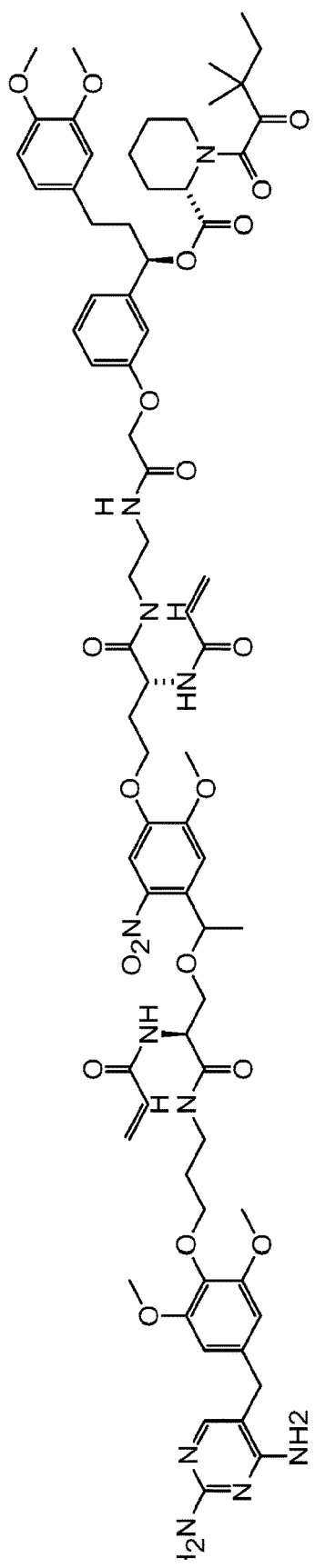
Figure 6D:
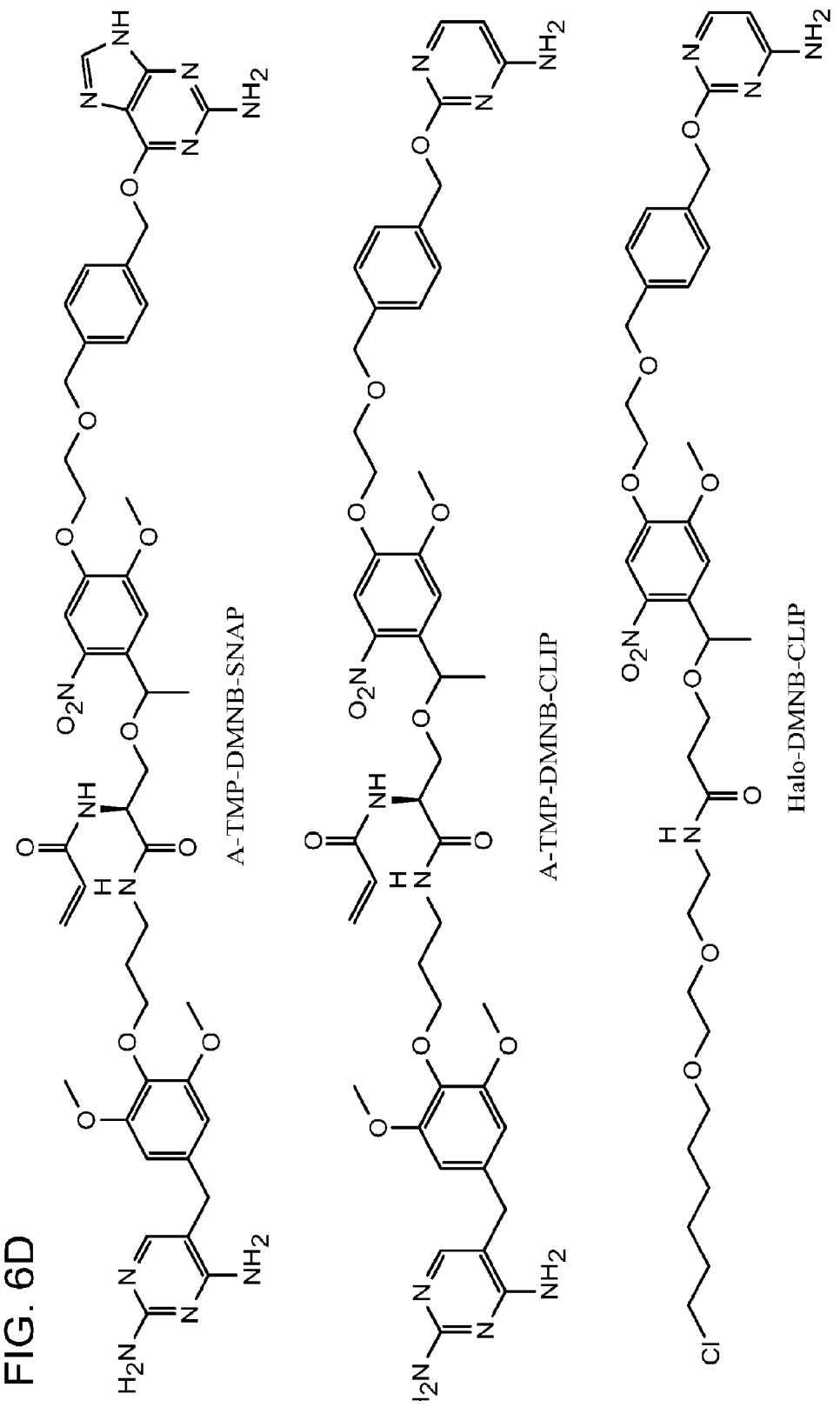

Preliminary tests of Zapalog efficacy in COS cells were also carried out, using a peroxisome translocation assay adapted from Kapitein et al., 2010 (13) and illustrated in FIG. 4. The FKBP domain is coupled to RFP and a peroxisome-binding domain (PEX). The DHFR domain is fused to the motor domain of the kinesin Kif 1a. In the absence of a CID to couple these two proteins, the peroxisomes are stationary and located near the nucleus while the motor (visualized by immunocytochemistry) is diffuse in the cytosol (FIG. 4 DMSO). Addition of either TMP-SLF or Zapalog (1 uM) in the dark caused the translocation of the motor domain to the peroxisomes and the redistribution of the peroxisomes to the periphery of the cell. However, whereas TMP-SLF was insensitive to light, exposure of Zapalog-treated cells to light caused the motor to detach from peroxisomes and resume its diffuse distribution as expected upon Zapalog photolysis (FIG. 4). In a live-imaging experiment (FIG. 5), the addition of Zapalog initiated clear movement of the peroxisomes in less than 2 minutes. The dispersal of peroxisomes was reversed by exposure to a 405 nm laser. These experiments establish several key points: 1) Zapalog is membrane permeable. 2) Zapalog is not toxic to cells. 3) Zapalog can bind to the DHFR and FKBP domains in vivo, i.e. the DMNB moiety did not interfere with binding. 4) Zapalog can cause heterodimerization, i.e. both DHFR and FKBP can bind simultaneously to Zapalog without steric interference. 5) the affinity of Zapalog in vivo is high enough to permit the transport of an organelle by a tethered motor. 6) Zapalog is photo-cleavable in vivo by 405 nm light. 7) Laser inactivation of Zapalog can be accomplished with energy levels that did not harm the cell. The experiments described herein seek to characterize Zapalog in sufficient detail to enable its use as a photo-cleavable CID. In particular, experiments were designed to determine the kinetics of Zapalog-induced dimerization and cleavage and whether it could be used to recreate a fully functional split kinesin for studies of motor interactions.

Example 2. Determination of Zapalog's Efficacy

Figure 7B:
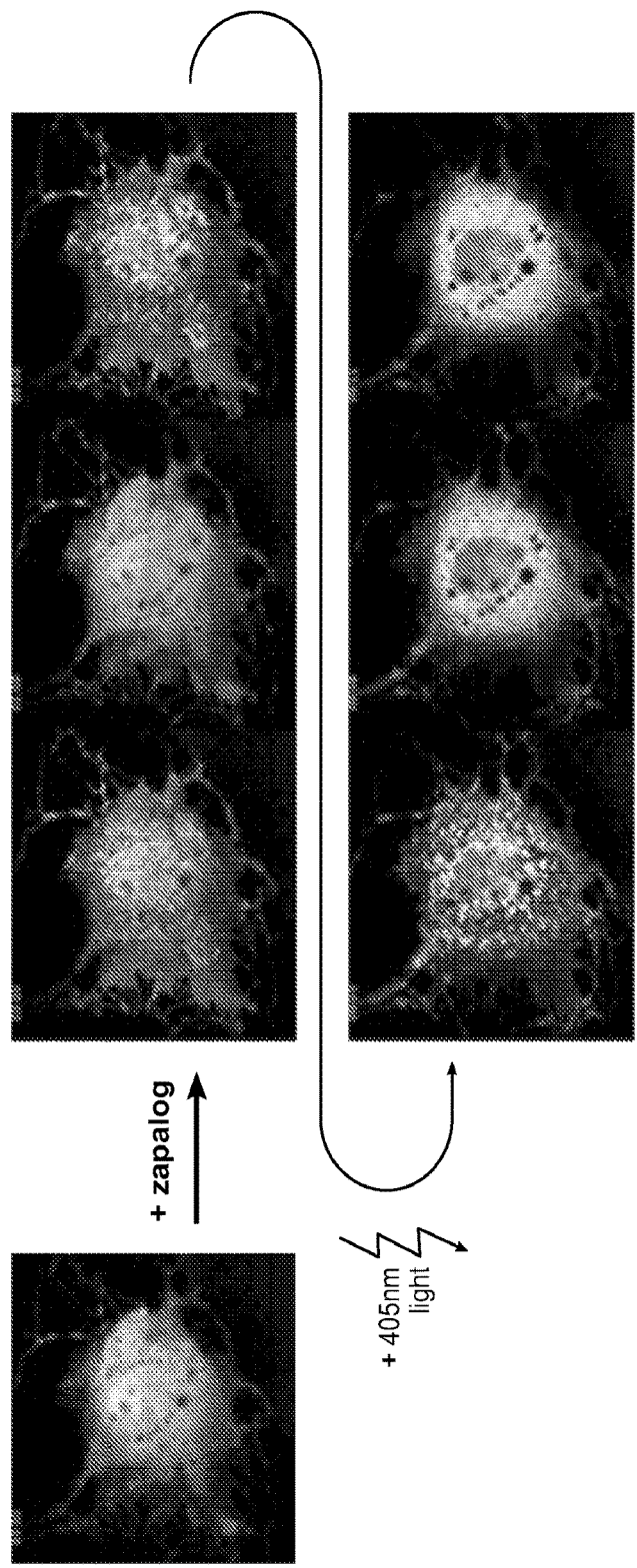
FIG. 7 shows a schematic diagram depicting a Zapalog efficacy assay, as described in detail below. Selected results of the efficacy assay are also shown.

In one set of experiments, Zapalog's efficacy as a dimerizing agent and the efficacy of light-induced cleavage was examined in simple assays of subcellular localization of a YFP reporter adapted from Komatsu et al., (Komatsu et al. Nature Methods 7: 206-8) and illustrated in FIG. 7 (optionally, a GFP or other reporter could have been used). An assay of Zapalog function was developed based on tethering a YFP reporter to the outer mitochondrial membrane of COST cells. In this assay, the YFP reporter was fused to the DHFR domain and, by default, was cytosolic. The FKBP domain was bound to the outer membrane of mitochondria with the N-terminus sequence of Tom20. The FKBP construct was tagged with mCherry. Addition of 1 µM Zapalog in the dark was shown to induce the relocalization of YFP to the mitochondrial surface within 4-5 minutes. Subsequent 405 nm illumination caused immediate (<5 sec) release of YFP back to the cytosol. This redistribution was followed in video microscopy and quantified as a ratio of membrane bound to cytoplasmic fluorescence intensity The peroxisome motility assay described above, while convenient for a quick look at Zapalog function, was not well suited to studying kinetics and concentration dependence because it depends on multiple parameters, including opposing motors, that govern peroxisome behavior in addition to the affinity of Zapalog for the target proteins and the efficiency of laser-induced photolysis. Further implementation of the YFP relocalization assay can be used to determine: (1) the optimal concentration range for Zapalog; (2) the speed with which Zapalog can induce dimerization; (3) the minimal laser power necessary to reverse the dimerization; and (4) the speed with which the dimerization can be reversed. These studies can also establish whether there is toxicity associated with either the necessary concentration of Zapalog or with the laser energy required for its photolysis. Moreover, these experiments represent a prototype for a class of experimental application in which a protein is first sequestered and then released, e.g. for translocation into the nucleus.

The principle of the translocation assay is straightforward. The assay is optionally performed in the dark or with a red safety light to avoid breakdown of Zapalog. Specific attention is paid to the stoichiometry of the three components of the translocation assay: the two binding domains and Zapalog. In certain embodiments, the membrane-bound FKBP is in excess to the YFP reporter so that it is not saturated. An optimal concentration for Zapalog is likely in the mid-nanomolar range based on what was found for TMP-SLF (9), and in view of the initial results of the above-described efficacy assay. Too little Zapalog would be insufficient to link all the DHFR and FKBP sites. Too high a concentration could also inhibit the linkage by saturating the two sites with separate ligands. Too high a concentration could also decrease the efficiency of the photolysis, if an unlysed percentage is sufficient to re-couple the reporter to the membrane. If the affinity of Zapalog is insufficient to completely restrict the YFP reporter to the membrane, methods of enhancing that affinity are tested as described in Example 3, below.

Example 3. Optimization of Zapalog

In another set of experiments, Zapalog will be optimized by examining variations in its structure and the composition of the receptors for Zapalog. The TMP and SLF ligands, independently, have affinities in the range of 1 nM which makes them highly effective in a CID (9). However, it is possible that the addition of the DMNB linker has decreased their affinity for their targets or that the off-rates of the ligand are still too high for some applications. To address these possibilities, two approaches will be used. The first is to replace SLF in Zapalog with a variant SLF' whose Kd for its partner, a mutated FKBP, is 0.094 nM (15). The resulting compound ("Zapalog 2.0") will be tested as in Example 1, above. Other variants could be prepared, including some that would form an irreversible covalent bond with their partner domains for optimal binding (see above).

A two-step photoactivation/photocleavage scheme could also be used. In this case, the photocleavable dimerizer is caged or inactive until exposed to long-wavelength light (450-500 nm) using a different chromophore than DMNB (e.g., RuBi or DEAC450, see FIG. 6). These long wavelengths do not activate or cleave DMNB. The now-activated photocleavable dimerizer triggers dimerization; this in situ activation is potentially much faster than administration of the active form of the dimerizer, and the active dimerizer can be localized with light activation (by local photoactivation and removal of the caging moiety).

The second approach will be to use tandem copies of either binding domain to greatly increase the affinity and decrease the dissociation rate of the two proteins. The most favorable partnering in the TMP-SLF study, for example, paired a single DHFR with 3 tandem FKBP domains (9). Inoue et al (8) used two tandem FKBP domains for a plasma membrane localizing site in a test of iRAP, and in a split kinesin assay (16), tandem FKBP domains were also optimal. The optimal arrangement of the binding domains may need to be determined for any given application and will depend both on the strength of the linkage formed and also on the influence of the added binding domains on the functioning of each component, i.e. a candidate protein would need to tolerate the inclusion of multiple DHFR or FKBP domains.

Example 4. Zapalog in Analysis of Axonal Transport

In another set of experiments, the suitability of Zapalog for analysis of axonal transport will be tested through a split kinesin assay in which cargo movement will depend on the presence of Zapalog to join the motor and cargo-binding domains of a kinesin. In this experiment, Zapalog will be applied to the study of axonal transport as a test of the photoinactivation concept and its suitability for neuroscience. Split kinesin molecules will be used because it has already been demonstrated by the Banker lab that they can be expressed as separate motor and cargo-binding domains and functionally reconstituted with rapalog (16). The long coiled-coil domains that normally couple these two halves of the motor will tolerate the insertion of the ligand-binding domains while preserving motor activity and cargo binding. As previously described, GFP-tagged transferrin receptors (TfR), a cargo normally directed overwhelmingly to the dendrites (17), could be misdirected into the axon if the cargo-binding domain of Kif13A or Kif13B was linked by a rapalog to the axon-directed motor domain of Kif5C (16). Equivalent constructs will be made, but using FKBP and DHFR domains on the component parts and Zapalog as the CID. Because Zapalog should have higher affinities for its binding partners than the CID used previously, it should also support axonal transport. It is predicted that fluorescent TfR-containing vesicles will be observed moving in axons only in the presence of Zapalog and that their anterograde movement can be halted with a 405 nM laser by uncoupling the motor portion from the cargo-binding protein. This assay will allow a close examination of the processivity of anterograde movement of the TfR vesicles which will give an important indication as to whether the off-rate of Zapalog is sufficiently slow to permit long-range continuous transport. It will also allow a determination of if the photolysis is sufficiently rapid to cause an abrupt change in transport.

Example 5—Use Zapalog to Investigate Motor Ensemble Behavior in *Aspergillus nidulans*

The filamentous fungus *Aspergillus nidulans* has been a valuable model organism for cell biology for over sixty years, having provided insights into fields ranging from metabolism to genetics, and more recently—intracellular trafficking[34,35]. *A. nidulans*' polarized hyphae contain long stretches of parallel microtubules whose plus ends uniformly point towards the hyphal tip. Similar to metazoan cells, many different cargos, including secretory vesicles, organelles and mRNA, are actively transported up and down these microtubules by the concerted efforts of dyneins and kinesins, in a system that has remained highly conserved throughout evolution[34]. Through its ability to thrive as either haploid or diploid, its fully sequenced genome, and its genetic tractability, *A. nidulans* presents an attractive experimental platform with which to manipulate motor proteins and tease apart their individual roles within the trafficking complex. Photo-destructible Kinesin-3 motors will be integrated into these cells' transport machinery by using established protocols for homologous recombination[36] to replace the endogenous kinesin-3 gene (UncA) with two transcripts encoding the kinesin-3 motor- and cargo binding halves, tethered to FKBP and DHFR domains. His will be done via two independent approaches: 1) Replacing kinesin-3 in one haploid strain with an FKBP-tagged kinesin-1 motor domain and in another with a DHFR-tagged cargo binding domain, then mating the two strains to generate a diploid that expresses both tagged Kinesin-3 halves. 2) Generating and recombining a bicistronic FKBP-T2A-DHFR construct into the endogenous kinesin-3 locus to generate a haploid strain that expresses a single bicistronic transcript under the endogenous promoter. As with the experiments proposed in cultured neurons (example 4), zapalog-induced photo-destructible kinesins will be targeted by light in order to uncover the immediate consequences of kinesin inactivation on anterograde- and retrograde-directed transport.

Equivalents

Those skilled in the art will recognize, or be able to ascertain using no more than routine experimentation, many equivalents to the specific embodiments of the invention described herein. Such equivalents are intended to be encompassed by the following claims.

Incorporation by Reference

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

REFERENCES

1. Hoffman-Kim D, Diefenbach T J, Eustace B K, Jay D G. Chromophore-assisted laser inactivation. Methods in cell biology. 2007; 82:335-54.
2. Guo J, Chen H, Puhl H L, 3rd, Ikeda SR. Fluorophore-assisted light inactivation produces both targeted and collateral effects on N-type calcium channel modulation in rat sympathetic neurons. J Physiol. 2006; 576(Pt 2):477-92.
3. Moglich A, Ayers R A, Moffat K. Addition at the molecular level: signal integration in designed Per-ARNT-Sim receptor proteins. Journal of Molecular Biology. 400(3): 477-86.
4. Lin M Z, Glenn J S, Tsien R Y. A drug-controllable tag for visualizing newly synthesized proteins in cells and whole animals. Proc Natl Acad Sci USA. 2008; 105(22):7744-9.
5. Spencer D M, Wandless Ti, Schreiber S L, Crabtree G R. Controlling signal transduction with synthetic ligands. Science. 1993; 262(5136):1019-24.
6. Belshaw P1, Ho S N, Crabtree G R, Schreiber S L. Controlling protein association and subcellular localization with a synthetic ligand that induces heterodimerization of proteins. Proc Natl Acad Sci USA. 1996; 93(10): 4604-7.
7. Clackson T. A stability switch for proteins. Chemistry & biology. 2006; 13(9):926-8.
8. Inoue T, Heo W D, Grimley 1S, Wandless T J, Meyer T. An inducible translocation strategy to rapidly activate and inhibit small GTPase signaling pathways. Nature methods. 2005; 2(6):415-8.
9. Czlapinski J L, Schelle M W, Miller L W, Laughlin S T, Kohler n, Cornish V W, Bertozzi C R. Conditional glycosylation in eukaryotic cells using a biocompatible chemical inducer of dimerization. Journal of the American Chemical Society. 2008; 130(40):13186-7.
10. Schwartz E A, Tachibana M. Electrophysiology of glutamate and sodium co-transport in a glial cell of the salamander retina. J Physiol. 1990; 426:43-80.
11. Lester H A, Nerbonne J M. Physiological and pharmacological manipulations with light flashes. Annual review of biophysics and bioengineering. 1982; 11:151-75.
12. Lancaster B, Hu H, Gibb B, Storm 1F. Kinetics of ion channel modulation by CAMP in rat hippocampal neurones. Physiol. 2006; 576(Pt 2):403-17.
13. Kapitein L C, Schlager M A, van der Zwan W A, Wulf P S, Keijzer N, Hoogenraad C C. Probing intracellular motor protein activity using an inducible cargo trafficking assay. Biophysical journal. 99(7):2143-52.
14. Zito K, Parnas 0, Fetter R D, Isacoff E Y, Goodman C S. Watching a synapse grow: noninvasive confocal imaging of synaptic growth in Drosophila. Neuron. 1999; 22(4):719-29.
15. Clackson T, Yang W, Rozamus L W, Hatada M, Amara 1F, Rollins C T, Stevenson L F, Magari S R, Wood S A, Courage N L, Lu X, Cerasoli F, Jr., Gilman M, Holt D A. Redesigning an FKBP-ligand interface to generate chemical dimerizers with novel specificity. Proc Natl Acad Sci USA. 1998; 95(18):10437-42.
16. Jenkins B, Decker H, Bentley M, Luisi J, Banker G. A novel split kinesin assay identifies motor proteins that interact with distinct vesicle populations. J Cell Biol. 2012; 198(4):749-61.
17. Jareb M, Banker G. The polarized sorting of membrane proteins expressed in cultured hippocampal neurons using viral vectors. Neuron. 1998; 20(5):855-67.
18. Derr N D, Goodman B S, Jungmann R, Leschziner A E, Shih W M, Reck-Peterson SL. Tug-of-war in motor protein ensembles revealed with a programmable DNA origami scaffold. Science. 338(6107):662-5.
19. Levi V, Serpinskaya A S, Gratton E, Gelfand V. Organelle transport along microtubules in Xenopus melanophores: evidence for cooperation between multiple motors. Biophysical journal. 2006; 90(1):318-27.
20. Soppina V, Rai A K, Ramaiya A.1, Barak P, Mallik R. Tug-of-war between dissimilar teams of microtubule motors regulates transport and fission of endosomes. Proc Natl Acad Sci USA. 2009; 106(46):19381-6.
21. Hendricks A G, Perlson E, Ross J L, Schroeder H W, 3rd, Tokito M, Holzbaur E L. Motor coordination via a tug-of-war mechanism drives bidirectional vesicle transport. Curr Biol.20(8):697-702.
22. Colin E, Zala D, Liot G, Rangone H, Borrell-Pages M, Li X J, Saudou F, Humbert S. Huntingtin phosphorylation acts as a molecular switch for anterograde/retrograde transport in neurons. Embo J. 2008; 27(15):2124-34.
23. Gross S P, Welte M A, Block S M, Wieschaus E F. Coordination of opposite-polarity microtubule motors. J Cell Biol. 2002; 156(4):715-24.
24. Leidel C, Longoria R A, Gutierrez F M, Shubeita G T. Measuring molecular motor forces in vivo: implications for tug-of-war models of bidirectional transport. Biophysical journal. 103 (3):492-500.
25. Kunwar A, Tripathy S K, Xu J, Mattson M K, Anand P, Sigua R, Vershinin M, McKenney R.1, Yu C C, Mogilner A, Gross S P. Mechanical stochastic tug-of-war models cannot explain bidirectional lipid-droplet transport. Proc Natl Acad Sci U 5 A. 108(47):18960-5.
26. Lath J A, Marin J A, Bloodgood R A, Guilford WI-I. The reciprocal coordination and mechanics of molecular motors in living cells. Proc Nati Acad Sci U 5 A. 2009; 106(9):3190-5.
27. Gross S P, Tuma M C, Deacon S W, Serpinskaya A S, Reilein A R, Gelfand V I. Interactions and regulation of molecular motors in Xenopus melanophores. J Cell Biol. 2002; 156(5):855-65.
28. Hallenbeck P J, Saxton W M. The axonal transport of mitochondria. J Cell Sci. 2005; 118(Pt 23):5411-9.
29. van Spronsen M, Mikhaylova M, Lipka J, Schlager M A, van den Heuvel D J, Kuijpers M, Wulf P S, Keijzer N, Demmers J, Kapitein L C, Jaarsma D, Gerritsen H C, Akhmanova A, Hoogenraad CC. TRAK/Milton Motor-Adaptor Proteins Steer Mitochondria Trafficking to Axons and Dendrites. Neuron. 2013; 77(3):485-502.
30. Pilling A D, Horiuchi 0, Lively C M, Saxton W M. Kinesin-1 and Dynein are the primary motors for fast transport of mitochondria in Drosophila motor axons. Mol Biol Cell. 2006; 17(4): 2057-68.
31. Haghnia M, Cavalli V, Shah S B, Schimmelpfeng K, Brusch R, Yang G, Herrera C, Pilling A, Goldstein L S. Dynactin is required for coordinated bidirectional motility, but not for dynein membrane attachment. Mol Biol Cell. 2007; 18(6):2081-9.
32. Lloyd T E, Machamer J, O'Hara K, Kim J H, Collins S E, Wong M Y, Sahin B, Imlach W, Yang Y, Levitan E S, McCabe B D, Kolodkin A L. The p150(Glued) CAP-Gly domain regulates initiation of retrograde transport at synaptic termini Neuron. 74(2):344-60.

33. Moughamian Al, Holzbaur E L. Dynactin is required for transport initiation from the distal axon. Neuron. 2012; 74(2):331-43.

34. Egan, M. J., McClintock, M. A. & Reck-Peterson, S. L. Microtubule-based transport in filamentous fungi. *Curr. Opin. Microbiol.* 15, 637-645 (2012).

35. Nayak, T. et al. A versatile and efficient gene-targeting system for *Aspergillus nidulans. Genetics* 172, 1557-1566 (2006).

36. Lloyd, T. E. et al. The p150(Glued) CAP-Gly domain regulates initiation of retrograde transport at synaptic termini *Neuron* 74, 344-360 (2012).

The contents of all patent, patent applications, and publication cited herein are incorporated herein by reference in their entireties.

What is claimed is:

1. A compound represented by the formula R¹—Y—R², wherein

R¹ is a ligand capable of selectively binding to a first receptor;

R² is a ligand capable of selectively binding to a second receptor;

Y is a linker providing a covalent linkage between R¹ and R², wherein Y is photocleavable;

R¹ is methotrexate, dexamethasone, 3,5,3'-triiodothyronine, trans-retinoic acid, biotin, coumermycin, tetracycline, lactose, FK506,

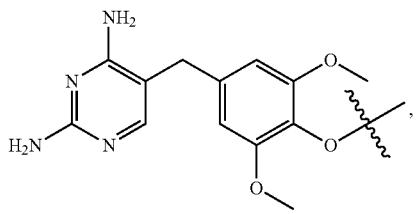 [SMILES: *Oc1c(OC)cc(Cc2cnc(N)nc2N)cc1OC]

analogs or derivatives thereof;

R² is

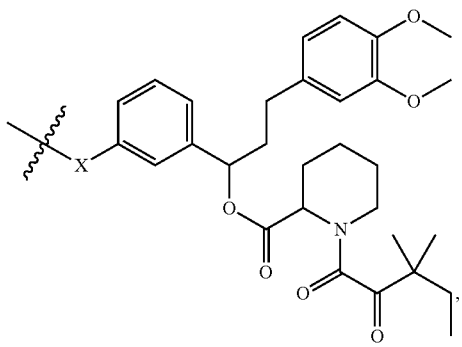

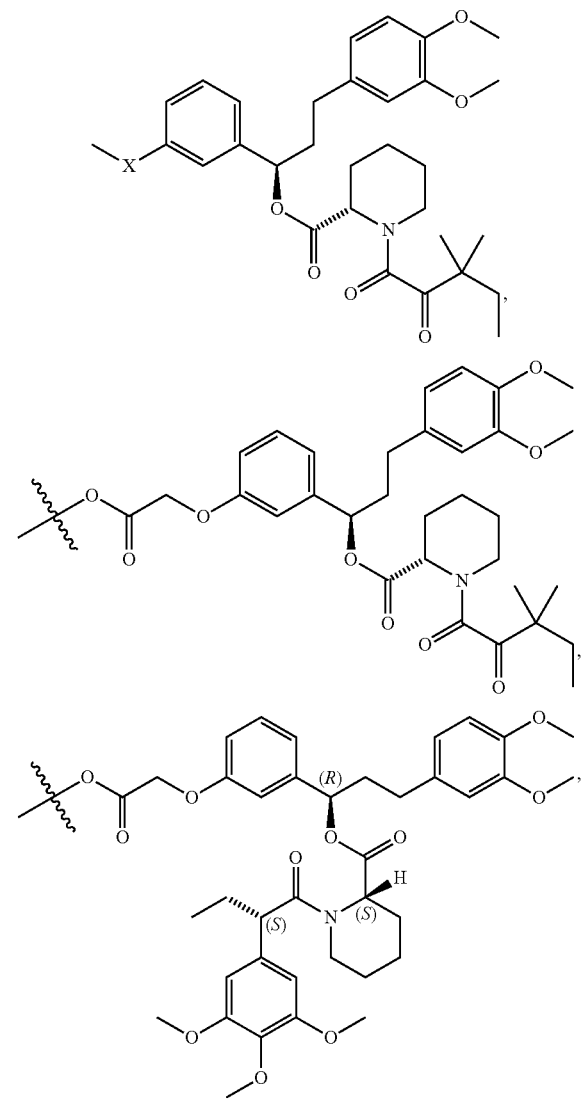

analogs or derivatives thereof, wherein X=O or NH;

Y is

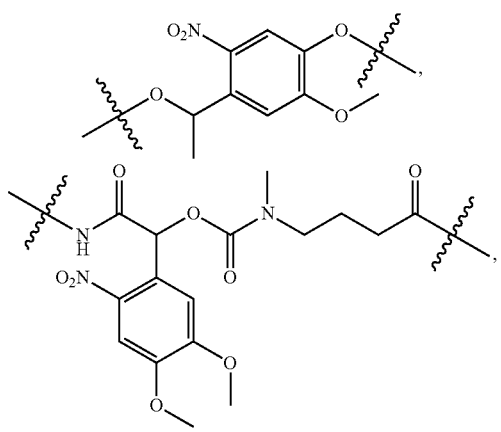

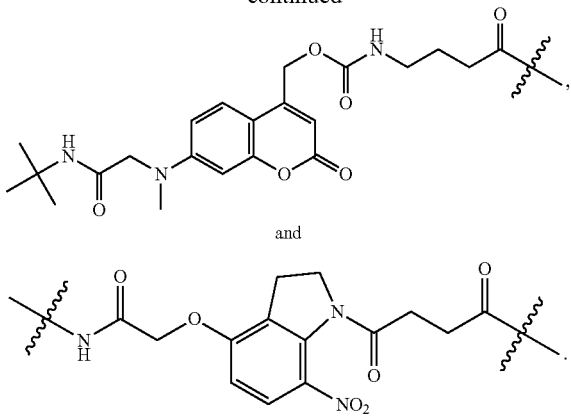

2. The compound of claim 1, wherein R¹ is a ligand capable of selectively binding to dihydrofolate reductase (DHFR).

3. The compound of claim 2, wherein the ligand capable of selectively binding to dihydrofolate reductase is trimethoprim (TMP) or a derivative or analog thereof, or methotrexate or a derivative or analog thereof.

4. The compound of claim 2, wherein R² is a ligand capable of selectively binding to FK506 Binding Protein (FKBP).

5. The compound of claim 4, wherein the ligand capable of selectively binding to FK506 Binding Protein (FKBP) is a synthetic ligand for FKBP (SLF) or a derivative or analog thereof.

6. The compound of claim 1, wherein Y is cleavable by exposure to light at a wavelength of about 405 nm.

7. The compound of claim 6, wherein Y comprises a dimethoxynitrobenzyl (DMNB) moiety or a derivative or analog thereof.

8. A complex comprising a compound of claim 1 complexed to (i) a first protein domain comprising a first binding domain and (ii) a second protein domain comprising a second binding domain.

9. A method of regulating activity of a protein, the method comprising:

(a) providing a complex comprising
 (i) a first protein domain comprising a first binding domain;
 (ii) a second protein domain comprising a second binding domain; and
 (iii) a compound of claim 1,
wherein the compound of claim 1 is bound to the first protein domain and the second protein domain;
(b) cleaving the compound of claim 1 by exposure to light, thereby cleaving the complex and regulating activity of the protein.

10. The method of claim 9, wherein the first binding domain is dihydrofolate reductase (DHFR).

11. The method of claim 10, wherein the DHFR is *E. coli* DHFR.

12. The method of claim 9, wherein the second binding domain is FK506 binding protein (FKBP).

13. The method of claim 9, wherein the first protein domain comprises one domain of an active protein.

14. The method of claim 9, wherein the second protein domain comprises another domain of an active protein.

15. The method of claim 9, wherein the first protein domain and the second protein domain together comprise a functional protein.

16. The method of claim 9, wherein regulating the activity of a protein comprises inactivating the protein.

17. The method of claim 9, wherein regulating the activity of a protein comprises activating the protein.

18. A method of regulating the activity of a protein in a cell, the method comprising:
(a) providing a cell that expresses a first protein domain comprising a first binding domain and a second protein domain that comprises a second binding domain;
(b) providing the compound of claim 1 that dimerizes the first and second protein domains; and
(c) cleaving the compound of claim 1 by exposure to light, thereby cleaving the complex and regulating activity of the protein.

19. The method of claim 18, wherein dimerization of the first and second protein domains produces an active protein.

20. The method of claim 18, wherein dimerization of the first and second protein domains inactivates the protein.

* * * * *

UNITED STATES PATENT AND TRADEMARK OFFICE
CERTIFICATE OF CORRECTION

| | |
|---|---|
| PATENT NO. | : 10,053,445 B2 |
| APPLICATION NO. | : 15/031628 |
| DATED | : August 21, 2018 |
| INVENTOR(S) | : Thomas L. Schwarz et al. |

It is certified that error appears in the above-identified patent and that said Letters Patent is hereby corrected as shown below:

In the Specification

At Column 1, Lines 22-25 reads:
"This work was supported by the following grant from the National Institutes of Health/National Institute of Neurological Disorders and Stroke: R21NS087582. The government has certain rights in the invention."

Should read:
--This invention was made with government support under Grant number NS087582, awarded by The National Institutes of Health. The government has certain rights in the invention.--

Signed and Sealed this
Eleventh Day of October, 2022

Katherine Kelly Vidal
Director of the United States Patent and Trademark Office